United States Patent
Kokoris et al.

(10) Patent No.: US 11,530,392 B2
(45) Date of Patent: Dec. 20, 2022

(54) DPO4 POLYMERASE VARIANTS WITH IMPROVED ACCURACY

(71) Applicant: STRATOS GENOMICS, INC., Seattle, WA (US)

(72) Inventors: Mark Kokoris, Bothell, WA (US); Marc Prindle, Seattle, WA (US); Gregory Scott Thiessen, Seattle, WA (US); Alexander Isaac Lehmann, Seattle, WA (US); Drew Goodman, Seattle, WA (US); Aaron Jacobs, Seattle, WA (US); John Chase, Seattle, WA (US)

(73) Assignee: Stratos Genomics, Inc., Seattle, WA (US)

( * ) Notice: Subject to any disclaimer, the term of this patent is extended or adjusted under 35 U.S.C. 154(b) by 0 days.

(21) Appl. No.: 16/770,923

(22) PCT Filed: Dec. 10, 2018

(86) PCT No.: PCT/US2018/064794
§ 371 (c)(1),
(2) Date: Jun. 8, 2020

(87) PCT Pub. No.: WO2019/118372
PCT Pub. Date: Jun. 20, 2019

(65) Prior Publication Data
US 2021/0163903 A1     Jun. 3, 2021

Related U.S. Application Data

(60) Provisional application No. 62/597,109, filed on Dec. 11, 2017, provisional application No. 62/656,696, filed on Apr. 12, 2018.

(51) Int. Cl.
*C12N 9/12*     (2006.01)

(52) U.S. Cl.
CPC .... *C12N 9/1252* (2013.01); *C12Y 207/07007* (2013.01)

(58) Field of Classification Search
None
See application file for complete search history.

(56) References Cited

U.S. PATENT DOCUMENTS

| | | |
|---|---|---|
| 5,432,272 A | 7/1995 | Benner |
| 6,150,510 A | 11/2000 | Seela et al. |
| 7,745,188 B2 | 6/2010 | Woodgate et al. |
| 7,939,259 B2 | 5/2011 | Kokoris et al. |
| 8,324,360 B2 | 12/2012 | Kokoris et al. |
| 8,999,676 B2 | 4/2015 | Emig et al. |
| 10,704,031 B2 | 7/2020 | Wu et al. |
| 10,745,685 B2 | 8/2020 | Kokoris et al. |
| 2014/0127694 A1 | 5/2014 | Holliger et al. |
| 2016/0304926 A1 | 10/2016 | Pech et al. |
| 2020/0385701 A1 | 12/2020 | Kokoris et al. |
| 2021/0108183 A1 | 4/2021 | Kokoris et al. |

FOREIGN PATENT DOCUMENTS

| | | |
|---|---|---|
| CN | 106318924 A | 1/2017 |
| WO | WO 9202258 A1 | 2/1992 |
| WO | WO 9310820 A1 | 6/1993 |
| WO | WO 9422892 A1 | 10/1994 |
| WO | WO 9424144 A2 | 10/1994 |
| WO | WO 2005113760 A2 | 12/2005 |
| WO | WO 2007076057 A2 | 7/2007 |
| WO | WO 2008051530 A2 | 5/2008 |
| WO | WO 2013170963 A2 | 11/2013 |
| WO | WO 2015074756 A1 | 5/2015 |
| WO | WO 2016081871 A1 | 5/2016 |
| WO | WO 2016183403 A2 | 11/2016 |
| WO | WO 2017087281 A1 | 5/2017 |
| WO | WO 2018204707 A1 | 11/2018 |
| WO | WO 2019118372 A1 | 6/2019 |

OTHER PUBLICATIONS

Ngo et al. in The Protein Folding Problem and Tertiary Structure Prediction, 1994, Merz et al. (ed.), Birkhauser, Boston, MA, pp. 433 and 492-495).*
Albà, "Protein family review: Replicative DNA polymerases" *Genome Biology*, 2(1):reviews3002.1-3002.4, 2001.
Beckman et al., "Kinetic Analysis of Correct Nucleotide Insertion by a Y-family DNA Polymerase Reveals Conformational Changes Both Prior to and following Phosphodiester Bond Formation as Detected by Tryptophan Fluorescence," *The Journal of Biological Chemistry* 283(52):36711-36723, 2008, (52 Pages).
Burgers et al., "Eukaryotic DNA Polymerases: Proposal for a Revised Nomenclature," *J. Biol. Chem.* 276(47):43487-43490, 2001.
Chen et al., "Reconstructed evolutionary adaptive paths give polymerases accepting reversible terminators for sequencing and SNP detection," *PNAS* 107(5):1948-1953, 2010.
Gardner et al., "Comparative Kinetics of Nucleotide Analog Incorporation by Vent DNA Polymerase," *J. Biol. Chem.* 279(12):11834-11842, 2004.
Gardner et al., "Determinants of nucleotide sugar recognition in an archaeon DNA polymerase," *Nucleic Acids Research* 27(12):2545-2553, 1999.

(Continued)

*Primary Examiner* — Richard G Hutson
(74) *Attorney, Agent, or Firm* — Kristen Walker

(57) ABSTRACT

Recombinant DPO4-type DNA polymerase variants with amino acid substitutions that confer modified properties upon the polymerase for improved single molecule sequencing applications are provided. Such properties may include enhanced binding and accurate incorporation of bulky nucleotide analog substrates into daughter strands and the like. Also provided are compositions comprising such DPO4 variants and nucleotide analogs, as well as nucleic acids which encode the polymerases with the aforementioned phenotypes.

6 Claims, 1 Drawing Sheet
Specification includes a Sequence Listing.

(56) References Cited

OTHER PUBLICATIONS

Goodman et al., "Translesion DNA Polymerases," *Cold Spring Harb. Perspect. Biol. 5*:a010363, 2013.
Hübscher et al., "Eukaryotic DNA Polymerases," *Annu. Rev. Biochem.* 77:133-163, 2002.
International Preliminary Report on Patentability, dated Jun. 16, 2020, for International Application No. PCT/US2018/064794, 8 pages.
International Preliminary Report on Patentability, dated Nov. 5, 2019, for International Application No. PCT/US2018/030972, 5 pages.
International Search Report and Written Opinion, dated Apr. 15, 2019, for International Application No. PCT/US2018/064794, 12 pages.
International Search Report and Written Opinion, dated Aug. 8, 2018, for International Application No. PCT/US2018/030972, 7 pages.
International Search Report and Written Opinion, dated Mar. 13, 2017, for International Application No. PCT/US2016/061661, 12 pages.
Kardashliev et al., "A High-Throughput Screening Method to Reengineer DNA Polymerases for Random Mutagenesis," *Mol. Biotechnol. 56*:274-283, 2014.
Ling et al., "Crystal Structure of a Y-Family DNA Polymerase in Action: A Mechanism for Error-Prone and Lesion-Bypass Replication," *Cell 107*:91-102, 2001.
McDonald et al., "Novel thermostable Y-family polymerases: applications for the PCR amplification of damaged or ancient DNAs," *Nucleic Acids Research 34*(4):1102-1111, 2006.
Pavelka et al., "HotSpot Wizard: a web server for identification of hot spots in protein engineering," *Nucleic Acids Research 37*:W376-W383, 2009.
Steitz, "DNA Polymerases: Structural Diversity and Common Mechanisms," *J. Biol. Chem. 274*(25):17395-17398, 1999.
UniProt, "DNA Polymerase IV," sequence ID No. D2PF68_SULID, downloaded Feb. 13, 2017, 2 pages.
UniProtKB, Accession No. M9U6J3, Jun. 26, 2013, URL=https://www.uniprot.org/uniprot/M9U6J3.txt.
Wang et al., "Increased Processivity, Misincorporation, and Nucleotide Incorporation Efficiency in Sulfobus solfataricus Dpo4 Thumb Domain Mutants," Appl. Environ. Microbiol. 83(18):1-13, 2017.
Xing et al., "Structural insight into recruitment of translesion DNA polymerase Dpo4 to sliding clamp PCNA" *Mol. Microbial. 71*(3):678-691, 2009.

* cited by examiner

```
  1
    M I V L F V D F D Y F Y A Q V E E V L N P S L K G K P V V V C V F S G R F E D S G A V A T A
              └─Mut1─┘                                    └─Mut2─┘      └──Mut13──┘
       10                    20                    30                    40

N Y E A R K F G V K A G I P I V E A K K I L P N A V Y L P M R K E V Y Q Q V S S R I M N L L
                  └──Mut3──┘                      └──Mut4──┘
       50                    60                    70                    80                    90

R E Y S E K I E I A S I D E A Y L D I S D K V R D Y R E A Y N L G L E I K N K I L E K E K I
    └────Mut5────┘
              100                   110                   120                   130

T V T V G I S K N K V F A K I A A D M A K P N G I K V I D D E E V K R L I R E L D I A D V P
                      └────Mut6────┘                              └─────Mut14─────┘ └──Mut7──┘
              140                   150                   160                   170                   180

G I G N I T A E K L K K L G I N K L V D T L S I E F D K L K G M I G E A K A K Y L I S L A R
    └─────Mut7─────┘                              └──────Mut8──────┘           └───
              190                   200                   210                   220                   230

D E Y N E P I R T R V R K S I G R I V T M K R N S R N L E E I K P Y L F R A I E E S Y Y K L
        └────Mut9────┘                                              └──────Mut15──────┘
              240                   250                   260                   270

D K R I P K A I H V V A V T E D L D I V S R G R T F P H G I S K E T A Y S E S V K L L Q K I
    └─Mut10─┘                └─────Mut11─────┘                  └─────Mut10─────┘
              280                   290                   300                   310                   320

L E E D E R K I R R I G V R F S K F I E A I G L D K F F D T
    └──────Mut12──────┘
              330                   340                   350
```

DPO4 POLYMERASE VARIANTS WITH IMPROVED ACCURACY

STATEMENT REGARDING SEQUENCE LISTING

The Sequence Listing associated with this application is provided in text format in lieu of a paper copy, and is hereby incorporated by reference into the specification. The name of the text file containing the Sequence Listing is 871225_421USPC_SEQUENCE_LISTING.txt. The text file is 100 KB, was created on Sep. 21, 2020, and is being submitted electronically via EFS-Web.

FIELD OF THE INVENTION

The disclosure relates generally to polymerase compositions and methods. More particularly, the disclosure relates to modified DPO4 polymerases and their use in biological and biomolecular applications including, for example, high-accuracy nucleotide analogue incorporation, primer-extension, and single molecule sequencing systems.

BACKGROUND OF THE INVENTION

DNA polymerases replicate the genomes of living organisms. In addition to this central role in biology, DNA polymerases are also ubiquitous tools of biotechnology. They are widely used, e.g., for reverse transcription, amplification, labeling, and sequencing, all central technologies for a variety of applications, such as nucleic acid sequencing, nucleic acid amplification, cloning, protein engineering, diagnostics, molecular medicine, and many other technologies.

Because of their significance, DNA polymerases have been extensively studied, with a focus, e.g., on phylogenetic relationships among polymerases, structure of polymerases, structure-function features of polymerases, and the role of polymerases in DNA replication and other basic biological processes, as well as ways of using DNA polymerases in biotechnology. Scientists have comprehensively catalogued DNA polymerases from all three kingdoms of life, with the enzymes being classified into six major families (A, B, C, D, X, and Y) according to their sequence homology. For a review of polymerases, see, e.g., Hubscher et al. (2002) "Eukaryotic DNA Polymerases" Annual Review of Biochemistry Vol. 71: 133-163, Alba (2001) "Protein Family Review: Replicative DNA Polymerases" Genome Biology 2(1): reviews 3002.1-3002.4, Steitz (1999) "DNA polymerases: structural diversity and common mechanisms" J Biol Chem 274:17395-17398, and Burgers et al. (2001) "Eukaryotic DNA polymerases: proposal for a revised nomenclature" J Biol. Chem. 276(47): 43487-90. Crystal structures have been solved for many polymerases, which often share a similar architecture. The basic mechanisms of action for many polymerases have been determined.

A fundamental application of DNA polymerases is in DNA sequencing technologies. From the classical Sanger sequencing method to recent "next-generation" sequencing (NGS) technologies, the nucleotide substrates used for sequencing have necessarily changed over time. The series of nucleotide modifications required by these rapidly changing technologies has introduced daunting tasks for DNA polymerase researchers to look for, design, or evolve compatible enzymes for ever-changing DNA sequencing chemistries. DNA polymerase mutants have been identified that have a variety of useful properties, including altered nucleotide analog incorporation abilities relative to wild-type counterpart enzymes. For example, $Vent^{A488L}$ DNA polymerase can incorporate certain non-standard nucleotides with a higher efficiency than native Vent DNA polymerase. See Gardner et al. (2004) "Comparative Kinetics of Nucleotide Analog Incorporation by Vent DNA Polymerase" J. Biol. Chem. 279(12):11834-11842 and Gardner and Jack (1999) "Determinants of nucleotide sugar recognition in an archaeon DNA polymerase" Nucleic Acids Research 27(12): 2545-2553. The altered residue in this mutant, A488, is predicted to be facing away from the nucleotide binding site of the enzyme. The pattern of relaxed specificity at this position roughly correlates with the size of the substituted amino acid side chain and affects incorporation by the enzyme of a variety of modified nucleotide sugars.

More recently, NGS technologies have introduced the need to adapt DNA polymerase enzymes to accept nucleotide substrates modified with reversible terminators on the 3'-OH, such as $-ONH_2$. To this end, Chen and colleagues combined structural analyses with a "reconstructed evolutionary adaptive path" analysis to generate a $TAQ^{L616A}$ variant that is able to efficiently incorporate both reversible and irreversible terminators. See Chen et al. (2010) "Reconstructed Evolutionary Adaptive Paths Give Polymerases Accepting Reversible Terminators for Sequencing and SNP Detection" Proc. Nat. Acad. Sci. 107(5):1948-1953. Modeling studies suggested that this variant might open space behind Phe-667, allowing it to accommodate the larger 3' substituents. U.S. Pat. No. 8,999,676 to Emig et al. discloses additional modified polymerases that display improved properties useful for single molecule sequencing technologies based on fluorescent detection. In particular, substitution of φ29 DNA polymerase at positions E375 and K512 was found to enhance the ability of the polymerase to utilize non-natural, phosphate-labeled nucleotide analogs incorporating different fluorescent dyes.

Recently, Kokoris et al. have described a method, termed "sequencing by expansion" (SBX), that uses a DNA polymerase to transcribe the sequence of DNA onto a measurable polymer called an Xpandomer (see, e.g., U.S. Pat. No. 8,324,360 to Kokoris et al.). The transcribed sequence is encoded along the Xpandomer backbone in high signal-to-noise reporters that are separated by ~10 nm and are designed for high signal-to-noise, well differentiated responses when read by nanopore-based sequencing systems. Xpandomers are generated from non-natural nucleotide analogs, termed XNTPs, characterized by bulky substituents that enable the Xpandomer backbone to be expanded following synthesis. Such XNTP analogs introduce novel challenges as substrates for currently available DNA polymerases. Published PCT application no. WO2017/087281 to Kokoris et al., herein incorporated by reference in its entirety, describes engineered DPO4 polymerase variants with enhanced primer extension activity utilizing non-natural, bulky nucleotide analogues as substrates.

Other challenges facing DNA polymerases are presented by certain nucleotide sequence motifs in the template. Of particular consequence are runs of homopolymers or short repeated DNA sequences that can trigger slipped-strand mispairing, or "replication slippage". Replication slippage is thought to encompass the following steps: (i) copying of the first repeat by the replication machinery, (ii) replication pausing and dissociation of the polymerase from the newly synthesized end, (iii) unpairing of the newly synthesized strand and its pairing with the second repeat, and (iv) resumption of DNA synthesis. Arrest of the replication machinery within a repeated region thus results in misalignment of primer and template. In vivo, misalignment of two DNA strands during replication can lead to DNA rearrangements such as deletions or duplications of varying lengths. In vitro, replication slippage results in replication errors at the site of the slippage event. Such reduction in polymerase accuracy significantly impairs the particular application or desired genetic manipulation.

Thus, new modified polymerases, e.g., polymerases engineered for improved properties that find use in sequencing by expansion (SBX) and other applications in biotechnology and biomedicine (e.g., DNA amplification, conventional sequencing, labeling, detection, cloning, etc.), would find value in the art as novel reagents. The present invention provides new recombinant DNA polymerases with such desirable properties, including the ability to incorporate nucleotide analogs with bulky substitutions with improved efficiency while demonstrating a reduction in the occurrence of replication errors, i.e., an increase in replication accuracy. Also provided are methods of making and using such polymerases, and many other features that will become apparent upon a complete review of the following.

SUMMARY

Recombinant DNA polymerases and modified DNA polymerases, e.g. modified archaeal DPO4, can find use in such applications as, e.g., single-molecule sequencing by expansion (SBX). Among other aspects, the invention provides recombinant DNA polymerases and modified DNA polymerase variants comprising mutations that confer properties, which can be particularly desirable for these applications. These properties can, e.g., 1) improve the ability of the polymerase to utilize bulky nucleotide analogs as substrates during template-dependent polymerization of a daughter strand and 2) increase the accuracy of nucleotide analog incorporation, particularly when the template includes nucleotide repeat sequences that can promote replication errors. Also provided are compositions comprising such DNA polymerases and modified DPO4-type polymerases, nucleic acids encoding such modified polymerases, methods of generating such modified polymerases and methods in which such polymerases can be used, e.g., to sequence a DNA template.

One general class of embodiments provides an isolated recombinant DNA polymerase having an amino acid sequence that is at least 80% identical to amino acids 1-340 of SEQ ID NO:1, and has a mutation at amino acid position 78, in which the mutation at amino acid 78 is K78D, and at least one mutation at an amino acid selected from the group consisting of 31, 36, 62, 63, 79, 243, 252, 253, 254, 331, 332, 334, and 338, wherein identification of positions is relative to wildtype DPO4 polymerase (SEQ ID NO:1), and which recombinant DNA polymerase exhibits polymerase activity. Another general class of embodiments provides an isolated recombinant DNA polymerase, having an amino acid sequence that is at least 85% identical to amino acids 1-340 of SEQ ID NO:1, and has a mutations at amino acid position 78, in which the mutation at amino acid 78 is K78D and at least one mutation at an amino acid selected from the group consisting of 31, 36, 62, 63, 79, 243, 252, 253, 254, 331, 332, 334, and 338. Exemplary mutations at positions 31, 36, 62, 63, 79, 243, 252, 253, 254, 331, 332, 334, and 338 include C31S, R36K, V62K, E63R, E79L, E79D, E79I, K243R, K252D, K252Q, K252R, R253Q, N254K, N254D, R331D, R331E, R331N, R331L, R332K, R332A, R332Q, R332S, G334N, G334Q, G334F, G334A, S338Y, and S338F. In some aspects, polymerases of the invention may also include at least one mutation at an amino acid position selected from the group consisting of 42, 56, 76, 82, 83, 86, 152, 153, 155, 156, 184, 187, 188, 189, 190, 248, 289, 290, 291, 292, 293, 294, 295, 296, 297, 299, 300, 301, 317, 321, 324, 325, and 327. Exemplary mutations at amino acid positions 42, 56, 76, 82, 83, 86, 152, 153, 155, 156, 184, 187, 188, 189, 190, 248, 289, 290, 291, 292, 293, 294, 295, 296, 297, 299, 300, 301, 317, 321, 324, 325, and 327 include A42V, K56Y, M76W, Q82W, Q83G, S86E, K152L or K152A, I153T or I153V, A155G, D156R, P184L or P184Q, G187P, N188Y, I189W or I189F, T190Y, I248T, V289W, T290K, E291S, D292Y, L293W, D294N, I295S, V296Q, S297Y, G299W, R300S, T301W, K317Q, K321Q, E324K, E325K, and E327K. In other embodiments, the recombinant DPO4-type DNA polymerase is represented by the amino acid sequence as set forth in any one of SEQ ID NOs: 3-34.

In a related aspect, the invention provides compositions containing any of the recombinant DPO4-type DNA polymerase set forth above. In certain embodiments, the compositions may also contain at least one non-natural nucleotide analog substrate.

In another related aspect, the invention provides modified nucleic acids encoding any of the modified DPO4-type DNA polymerase set forth above.

BRIEF DESCRIPTION OF THE FIGURES

FIG. 1 shows the amino acid sequence of the DPO4 polymerase protein (SEQ ID NO:1) with the Mut_1 through Mut_15 regions outlined and variable amino acids underscored.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

The term "about" as used herein indicates the value of a given quantity varies by +/−10% of the value, or optionally +/−5% of the value, or in some embodiments, by +/−1% of the value so described.

"Nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT Publication Nos. WO 92/002258, WO 93/10820, WO 94/22892, and WO 94/24144, and Fasman ("Practical Handbook of Biochemistry and Molecular Biology", pp. 385-394, 1989, CRC Press, Boca Raton, La.), all herein incorporated by reference in their entireties.

"Nucleobase residue" includes nucleotides, nucleosides, fragments thereof, and related molecules having the property of binding to a complementary nucleotide. Deoxynucleotides and ribonucleotides, and their various analogs, are contemplated within the scope of this definition. Nucleobase residues may be members of oligomers and probes. "Nucleobase" and "nucleobase residue" may be used interchangeably herein and are generally synonymous unless context dictates otherwise.

"Polynucleotides", also called nucleic acids, are covalently linked series of nucleotides in which the 3' position of the pentose of one nucleotide is joined by a phosphodiester group to the 5' position of the next. DNA (deoxyribonucleic acid) and RNA (ribonucleic acid) are biologically occurring polynucleotides in which the nucleotide residues are linked in a specific sequence by phosphodiester linkages. As used herein, the terms "polynucleotide" or "oligonucleotide" encompass any polymer compound having a linear backbone of nucleotides. Oligonucleotides, also termed oligomers, are generally shorter chained polynucleotides.

"Nucleic acid" is a polynucleotide or an oligonucleotide. A nucleic acid molecule can be deoxyribonucleic acid (DNA), ribonucleic acid (RNA), or a combination of both. Nucleic acids are generally referred to as "target nucleic acids" or "target sequence" if targeted for sequencing. Nucleic acids can be mixtures or pools of molecules targeted for sequencing.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide polymer, rather than by the actual position of the component in the given polymer. Similarly, identification of a given position within a given amino acid or nucleotide polymer is "relative to" a selected amino acid or nucleotide polymer when the position of any given polymer component (amino acid residue, incorporated nucleotide, etc.) is designated by reference to the residue name and position in the selected amino acid or nucleotide polymer, rather than by the actual name and position of the component in the given polymer. Correspondence of positions is typically determined by aligning the relevant amino acid or polynucleotide sequences.

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is, e.g., a polypeptide or protein which is produced by expression of a recombinant nucleic acid.

A "DPO4-type DNA polymerase" is a DNA polymerase naturally expressed by the archaea, *Sulfolobus solfataricus*, or a related Y-family DNA polymerase, which generally function in the replication of damaged DNA by a process known as translesion synthesis (TLS). Y-family DNA polymerases are homologous to the DPO4 polymerase (e.g., as listed in SEQ ID NO:1); examples include the prokaryotic enzymes, PolII, PolIV, PolV, the archaeal enzyme, Dbh, and the eukaryotic enzymes, Rev3p, Rev1p, Pol η, REV3, REV1, Pol I, and Pol κ DNA polymerases, as well as chimeras thereof. A modified recombinant DPO4-type DNA polymerase includes one or more mutations relative to naturally-occurring wild-type DPO4-type DNA polymerases, for example, one or more mutations that increase the ability to utilize bulky nucleotide analogs as substrates or another polymerase property, and may include additional alterations or modifications over the wild-type DPO4-type DNA polymerase, such as one or more deletions, insertions, and/or fusions of additional peptide or protein sequences (e.g., for immobilizing the polymerase on a surface or otherwise tagging the polymerase enzyme).

"Template-directed synthesis", "template-directed assembly", "template-directed hybridization", "template-directed binding" and any other template-directed processes, e.g., primer extension, refers to a process whereby nucleotide residues or nucleotide analogs bind selectively to a complementary target nucleic acid, and are incorporated into a nascent daughter strand. A daughter strand produced by a template-directed synthesis is complementary to the single-stranded target from which it is synthesized. It should be noted that the corresponding sequence of a target strand can be inferred from the sequence of its daughter strand, if that is known. "Template-directed polymerization" is a special case of template-directed synthesis whereby the resulting daughter strand is polymerized.

"XNTP" is an expandable, 5' triphosphate modified nucleotide substrate compatible with template dependent enzymatic polymerization. An XNTP has two distinct functional components; namely, a nucleobase 5'-triphosphate and a tether or tether precursor that is attached within each nucleotide at positions that allow for controlled RT expansion by intra-nucleotide cleavage.

"Xpandomer intermediate" is an intermediate product (also referred to herein as a "daughter strand") assembled from XNTPs, and is formed by a template-directed assembly of XNTPs using a target nucleic acid template. The Xpandomer intermediate contains two structures; namely, the constrained Xpandomer and the primary backbone. The constrained Xpandomer comprises all of the tethers in the daughter strand but may comprise all, a portion or none of the nucleobase 5'-triphosphates as required by the method. The primary backbone comprises all of the abutted nucleobase 5'-triphosphates. Under the process step in which the primary backbone is fragmented or dissociated, the constrained Xpandomer is no longer constrained and is the Xpandomer product which is extended as the tethers are stretched out. "Duplex daughter strand" refers to an Xpandomer intermediate that is hybridized or duplexed to the target template.

"Xpandomer" or "Xpandomer product" is a synthetic molecular construct produced by expansion of a constrained Xpandomer, which is itself synthesized by template-directed assembly of XNTPs. The Xpandomer is elongated relative to the target template it was produced from. It is composed of a concatenation of XNTPs, each XNTP including a tether comprising one or more reporters encoding sequence information. The Xpandomer is designed to expand to be longer than the target template thereby lowering the linear density of the sequence information of the target template along its length. In addition, the Xpandomer optionally provides a platform for increasing the size and abundance of reporters which in turn improves signal to noise for detection. Lower linear information density and stronger signals increase the resolution and reduce sensitivity requirements to detect and decode the sequence of the template strand.

"Tether" or "tether member" refers to a polymer or molecular construct having a generally linear dimension and with an end moiety at each of two opposing ends. A tether is attached to a nucleobase 5'-triphosphate with a linkage in at least one end moiety to form an XNTP. The end moieties of the tether may be connected to cleavable linkages to the nucleobase 5'-triphosphate that serve to constrain the tether in a "constrained configuration". After the daughter strand is synthesized, each end moiety has an end linkage that couples directly or indirectly to other tethers. The coupled tethers comprise the constrained Xpandomer that further comprises the daughter strand. Tethers have a "constrained configuration" and an "expanded configuration". The constrained configuration is found in XNTPs and in the daughter strand. The constrained configuration of the tether is the precursor to the expanded configuration, as found in Xpandomer products. The transition from the constrained configuration to the expanded configuration results cleaving of selectively cleavable bonds that may be within the primary backbone of the daughter strand or intra-tether linkages. A tether in a constrained configuration is also used where a tether is added to form the daughter strand after assembly of the "primary backbone". Tethers can optionally comprise one or more reporters or reporter constructs along its length that can encode sequence information of substrates. The tether provides a means to expand the length of the Xpandomer and thereby lower the sequence information linear density.

"Tether element" or "tether segment" is a polymer having a generally linear dimension with two terminal ends, where the ends form end-linkages for concatenating the tether elements. Tether elements may be segments of tether constructs. Such polymers can include, but are not limited to: polyethylene glycols, polyglycols, polypyridines, polyisocyanides, polyisocyanates, poly(triarylmethyl)methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments.

A variety of additional terms are defined or otherwise characterized herein.

DETAILED DESCRIPTION

One aspect of the invention is generally directed to compositions comprising a recombinant polymerase, e.g., a recombinant DPO4-type DNA polymerase that includes one or more mutations as compared to a reference polymerase, e.g., a wildtype DPO4-type polymerase. Depending on the particular mutation or combination of mutations, the polymerase exhibits one or more properties that find use, e.g., in single molecule sequencing applications. Exemplary properties exhibited by various polymerases of the invention include the ability to incorporate "bulky" nucleotide analogs into a growing daughter strand during DNA replication with improved efficiency and accuracy relative to known polymerases. The polymerases can include one or more exogenous or heterologous features at the N- and/or C-terminal regions of the protein for use, e.g., in the purification of the recombinant polymerase. The polymerases can also include one or more deletions that facilitate purification of the protein, e.g., by increasing the solubility of recombinantly produced protein.

These new polymerases are particularly well suited to DNA replication and/or sequencing applications, particularly sequencing protocols that include incorporation of bulky nucleotide analogs into a replicated nucleic acid daughter strand, such as in the sequencing by expansion (SBX) protocol, as further described below.

Polymerases of the invention include, for example, a recombinant DPO4-type DNA polymerase that has the mutation K78D, and at least one additional mutation at an amino acid selected from the group consisting of 31, 36, 62, 63, 79, 252, 243, 253, 254, 331, 332, 334, and 338 in which identification of positions is relative to wild-type DPO4 polymerase (SEQ ID NO:1). The polymerase may also have mutations at least one amino acid position selected from the group consisting of 42, 56, 76, 82, 83, 86, 152, 153, 155, 156, 184, 187, 188, 189, 190, 248, 289, 290, 291, 292, 293, 294, 295, 296, 297, 299, 300, 301, 317, 321, 324, 325, and 327. The polymerase may comprise mutations at 16 or more, up to 20 or more, up to 30 or more, up to 40 or more, more of these positions. The polymerases of the invention may also possess a deletion of amino acids 341-352 of the wildtype protein, corresponding to the "PIP box". In some embodiments, the polymerases of the invention may include mutations at additional residues not cited herein, provided that such mutations provide functional advantages as discussed further herein. In certain embodiments the polymerases of the invention are at least 80% identical to SEQ ID NO:1 (amino acids 1-340 of wildtype DPO4 DNA polymerase. In other embodiments, the polymerases of the invention may be less than 80% identical to SEQ ID NO:1, provided that such polymerases demonstrate enhanced abilities to utilize XNTPs as polymerization substrates. A number of exemplary substitutions at these (and other) positions are described herein.

DNA Polymerases

DNA polymerases that can be modified to increase the ability to incorporate bulky nucleotide analog substrates into a growing daughter nucleic acid strand and/or other desirable properties as described herein are generally available. DNA polymerases are sometimes classified into six main groups, or families, based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol. Chem. 276(47): 43487-90. For a review of polymerases, see, e.g., Hubscher et al. (2002) "Eukaryotic DNA Polymerases" Annual Review of Biochemistry Vol. 71: 133-163; Alba (2001) "Protein Family Review: Replicative DNA Polymerases" Genome Biology 2(1): reviews 3002.1-3002.4; and Steitz (1999) "DNA polymerases: structural diversity and common mechanisms" J Biol Chem 274:17395-17398. DNA polymerase have been extensively studied and the basic mechanisms of action for many have been determined. In addition, the sequences of literally hundreds of polymerases are publicly available, and the crystal structures for many of these have been determined or can be inferred based upon similarity to solved crystal structures for homologous polymerases. For example, the crystal structure of DPO4, a preferred type of parental enzyme to be modified according to the present invention, is available see, e.g., Ling et al. (2001) "Crystal Structure of a Y-Family DNA Polymerase in Action: A Mechanism for Error-Prone and Lesion-Bypass Replication" Cell 107:91-102.

DNA polymerases that are preferred substrates for mutation to increase the use of bulky nucleotide analog as substrates for incorporation into growing nucleic acid daughter strands, and/or to alter one or more other property described herein include DPO4 polymerases and other members of the Y family of translesional DNA polymerases, such as Dbh, and derivatives of such polymerases.

In one aspect, the polymerase that is modified is a DPO4-type DNA polymerase. For example, the modified recombinant DNA polymerase can be homologous to a wildtype DPO4 DNA polymerase. Alternately, the modified recombinant DNA polymerase can be homologous to other Class Y DNA polymerases, also known as "translesion" DNA polymerases, such as *Sulfolobus acidocaldarius* Dbh polymerase. For a review, see Goodwin and Woodgate (2013) "Translesion DNA Polymerases" Cold Spring Harb Perspect in Biol doi:10.1101/cshperspect.a010363. See, e.g., SEQ ID NO:1 for the amino acid sequence of wildtype DPO4 polymerase.

In other aspects, the polymerase that is modified is a DNA Pol Kappa-type polymerase, a DNA Pol Eta-type polymerase, a PrimPol-type polymerase, or a Terminator Gamma-type polymerase derived from any suitable species, such as yeast, human, *S. islandicus*, or *T. thermophilus*. The polymerase that is modified may be full length or truncated versions that include or lack various features of the protein. Certain desired features of these polymerases may also be combined with any of the DPO4 variants disclosed herein.

Many polymerases that are suitable for modification, e.g., for use in sequencing technologies, are commercially available. For example, DPO4 polymerase is available from TREVEGAN® and New England Biolabs®.

In addition to wildtype polymerases, chimeric polymerases made from a mosaic of different sources can be used. For example, DPO4-type polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple DPO4-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. Appropriate mutations to improve incorporation of bulky nucleotide analog substrates or another desirable property can be introduced into the chimeras.

Nucleotide Analogs

As discussed, various polymerases of the invention can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

Many nucleotide analogs are available and can be incorporated by the polymerases of the invention. These include analog structures with core similarity to naturally occurring nucleotides, such as those that comprise one or more substituent on a phosphate, sugar, or base moiety of the nucleoside or nucleotide relative to a naturally occurring nucleoside or nucleotide.

In one useful aspect of the invention, nucleotide analogs can also be modified to achieve any of the improved properties desired. For example, various tethers, linkers, or other substituents can be incorporated into analogs to create a "bulky" nucleotide analog, wherein the term "bulky" is understood to mean that the size of the analog is substantially larger than a natural nucleotide, while not denoting any particular dimension. For example, the analog can include a substituted compound (i.e., a "XNTP", as disclosed in U.S. Pat. No. 7,939,259 and PCT Publication No. WO 2016/081871 to Kokoris et al.) of the formula:

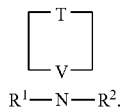

As shown in the above formula, the monomeric XNTP construct has a nucleobase residue, N, that has two moieties separated by a selectively cleavable bond (V), each moiety attaching to one end of a tether (T). The tether ends can attach to the linker group modifications on the heterocycle, the ribose group, or the phosphate backbone. The monomer substrate also has an intra-substrate cleavage site positioned within the phosphororibosyl backbone such that cleavage will provide expansion of the constrained tether. For example, to synthesize a XATP monomer, the amino linker on 8-[(6-Amino)hexyl]-amino-ATP or N6-(6-Amino)hexyl-ATP can be used as a first tether attachment point, and a mixed backbone linker, such as the non-bridging modification (N-1-aminoalkyl) phosphoramidate or (2-aminoethyl) phosphonate, can be used as a second tether attachment point. Further, a bridging backbone modification such as a phosphoramidate (3' O--P--N 5') or a phosphorothiolate (3' O--P--S 5'), for example, can be used for selective chemical cleavage of the primary backbone. $R^1$ and $R^2$ are end groups configured as appropriate for the synthesis protocol in which the substrate construct is used. For example, $R^1$=5'-triphosphate and $R^2$=3'-OH for a polymerase protocol. The $R^1$ 5' triphosphate may include mixed backbone modifications, such as an aminoethyl phosphonate or 3'-O--P--S-5' phosphorothiolate, to enable tether linkage and backbone cleavage, respectively. Optionally, $R^2$ can be configured with a reversible blocking group for cyclical single-substrate addition. Alternatively, $R^1$ and $R^2$ can be configured with linker end groups for chemical coupling. $R^1$ and $R^2$ can be of the general type XR, wherein X is a linking group and R is a functional group. Detailed atomic structures of suitable substrates for polymerase variants of the present invention may be found, e.g., in Vaghefi, M. (2005) "Nucleoside Triphosphates and their Analogs" CRC Press Taylor & Francis Group.

Applications for Enhanced Ability to Accurately Incorporate Bulky Nucleotide Analog Substrates Polymerases of the invention, e.g., modified recombinant polymerases, or variants, may be used in combination with nucleotides and/or nucleotide analogs and nucleic acid templates (DNA or RNA) to copy the template nucleic acid. That is, a mixture of the polymerase, nucleotides/analogs, and optionally other appropriate reagents, the template and a replication initiating moiety (e.g., primer) is reacted such that the polymerase synthesizes a daughter nucleic acid strand (e.g., extends the primer) in a template-dependent manner. The replication initiating moiety can be a standard oligonucleotide primer, or, alternatively, a component of the template, e.g., the template can be a self-priming single stranded DNA, a nicked double stranded DNA, or the like. Similarly, a terminal protein can serve as an initiating moiety. At least one nucleotide analog can be incorporated into the DNA. The template DNA can be a linear or circular DNA, and in certain applications, is desirably a circular template (e.g., for rolling circle replication or for sequencing of circular templates). Optionally, the composition can be present in an automated DNA replication and/or sequencing system.

In one embodiment, the daughter nucleic acid strand is an Xpandomer intermediate comprised of XNTPs, as disclosed in U.S. Pat. No. 7,939,259, and PCT Publication No. WO 2016/081871 to Kokoris et al. and assigned to Stratos Genomics, which are herein incorporated by reference in their entirety. Stratos Genomics has developed a method called Sequencing by Expansion ("SBX") that uses a DNA polymerase to transcribe the sequence of DNA onto a measurable polymer called an "Xpandomer". In general terms, an Xpandomer encodes (parses) the nucleotide sequence data of the target nucleic acid in a linearly expanded format, thereby improving spatial resolution, optionally with amplification of signal strength. The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. Xpandomers can enable several next generation DNA sequencing technologies and are well suited to nanopore sequencing. As discussed above, one method of Xpandomer synthesis uses XNTPs as nucleic acid analogs to extend the template-dependent synthesis and uses a DNA polymerase variant as a catalyst.

Mutating Polymerases

Various types of mutagenesis are optionally used in the present invention, e.g., to modify polymerases to produce variants, e.g., in accordance with polymerase models and model predictions as discussed above, or using random or semi-random mutational approaches. In general, any available mutagenesis procedure can be used for making polymerase mutants. Such mutagenesis procedures optionally include selection of mutant nucleic acids and polypeptides for one or more activity of interest (e.g., the ability to incorporate bulky nucleotide analogs into a daughter nucleic acid strand). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including wild-type DPO4 polymerase.

Optionally, mutagenesis can be guided by known information (e.g., "rational" or "semi-rational" design) from a naturally occurring polymerase molecule, or of a known altered or mutated polymerase (e.g., using an existing mutant polymerase as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291.

Additional information on mutation formats is found in: Sambrook et al., Molecular Cloning—A Laboratory Manual (3rd Ed.), Vol. 1-3, Cold Spring Harbor Laboratory, Cold Spring Harbor, N.Y., 2000 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 2011) ("Ausubel")) and PCR Protocols A Guide to Methods and Applications (Innis et al. eds) Academic Press Inc. San Diego, Calif. (1990) ("Innis"). The following publications and references cited within provide additional detail on mutation formats: Arnold, Protein engineering for unusual environments, Current Opinion in Biotechnology 4:450-455 (1993); Bass et al., Mutant Trp repressors with new DNA-binding specificities, Science 242:240-245 (1988); Bordo and Argos (1991) Suggestions for "Safe" Residue Substitutions in Site-directed Mutagenesis 217:721-729; Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14: 5115 (1986); Fritz et al., Oligonucleotide-directed construction of mutations: a gapped duplex DNA procedure without enzymatic reactions in vitro, Nucl. Acids Res. 16: 6987-6999 (1988); Grundstrom et al., Oligonucleotide-directed mutagenesis by microscale 'shot-gun' gene synthesis, Nucl. Acids Res. 13: 3305-3316 (1985); Hayes (2002) Combining Computational and Experimental Screening for rapid Optimization of Protein Properties PNAS 99(25) 15926-15931; Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al., Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of *Escherichia coli*: a method for site-specific mutagenesis, Proc. Natl. Acad. Sci. USA, 83:7177-7181(1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301(1984); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462 (1985); Methods in Enzymol. 100: 468-500 (1983); Methods in Enzymol. 154: 329-350 (1987); Stemmer, Nature 370, 389-91(1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M 13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Screening Polymerases

Screening or other protocols can be used to determine whether a polymerase displays a modified activity, e.g., for a nucleotide analog, as compared to a parental DNA polymerase. For example, the ability to bind and incorporate bulky nucleotide analogs into a daughter strand during template-dependent DNA synthesis. Assays for such properties, and the like, are described herein. Performance of a recombinant polymerase in a primer extension reaction can be examined to assay properties such as nucleotide analog incorporations etc., as described herein.

In one desirable aspect, a library of recombinant DNA polymerases can be made and screened for these properties. For example, a plurality of members of the library can be made to include one or more mutation that alters incorporations and/or randomly generated mutations (e.g., where different members include different mutations or different combinations of mutations), and the library can then be screened for the properties of interest (e.g., incorporations, etc.). In general, the library can be screened to identify at least one member comprising a modified activity of interest.

Libraries of polymerases can be either physical or logical in nature. Moreover, any of a wide variety of library formats can be used. For example, polymerases can be fixed to solid surfaces in arrays of proteins. Similarly, liquid phase arrays of polymerases (e.g., in microwell plates) can be constructed for convenient high-throughput fluid manipulations of solutions comprising polymerases. Liquid, emulsion, or gel-phase libraries of cells that express recombinant polymerases can also be constructed, e.g., in microwell plates, or on agar plates. Phage display libraries of polymerases or polymerase domains (e.g., including the active site region or interdomain stability regions) can be produced. Likewise, yeast display libraries can be used. Instructions in making and using libraries can be found, e.g., in Sambrook, Ausubel and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. RainDance Technologies' nanodroplet platform provides another method for handling large numbers of spatially separated reactions. Furthermore, the patent and technical literature includes many examples of microfluidic systems which can interface directly with microwell plates for fluid handling.

Tags and Other Optional Polymerase Features

The recombinant DNA polymerase optionally includes additional features exogenous or heterologous to the polymerase. For example, the recombinant polymerase optionally includes one or more tags, e.g., purification, substrate binding, or other tags, such as a polyhistidine tag, a His10 tag, a His6 tag, an alanine tag, an Ala16 tag, an Ala16 tag, a biotin tag, a biotin ligase recognition sequence or other biotin attachment site (e.g., a BiTag or a Btag or variant thereof, e.g., BtagV1-11), a GST tag, an S Tag, a SNAP-tag, an HA tag, a DSB (Sso7D) tag, a lysine tag, a NanoTag, a Cmyc tag, a tag or linker comprising the amino acids glycine and serine, a tag or linker comprising the amino acids glycine, serine, alanine and histidine, a tag or linker comprising the amino acids glycine, arginine, lysine, glutamine and proline, a plurality of polyhistidine tags, a plurality of His10 tags, a plurality of His6 tags, a plurality of alanine tags, a plurality of Ala10 tags, a plurality of Ala16 tags, a plurality of biotin tags, a plurality of GST tags, a plurality of BiTags, a plurality of S Tags, a plurality of SNAP-tags, a plurality of HA tags, a plurality of DSB (Sso7D) tags, a plurality of lysine tags, a plurality of NanoTags, a plurality of Cmyc tags, a plurality of tags or linkers comprising the amino acids glycine and serine, a plurality of tags or linkers comprising the amino acids glycine, serine, alanine and histidine, a plurality of tags or linkers comprising the amino acids glycine, arginine, lysine, glutamine and proline, biotin, avidin, an antibody or antibody domain, antibody fragment, antigen, receptor, receptor domain, receptor fragment, or ligand, one or more protease site (e.g., Factor Xa, enterokinase, or thrombin site), a dye, an acceptor, a quencher, a DNA binding domain (e.g., a helix-hairpin-helix domain from topoisomerase V), or combination thereof. The one or more exogenous or heterologous features at the N- and/or C-terminal regions of the polymerase can find use not only for purification purposes, immobilization of the polymerase to a substrate, and the like, but can also be useful for altering one or more properties of the polymerase.

The one or more exogenous or heterologous features can be included internal to the polymerase, at the N-terminal region of the polymerase, at the C-terminal region of the polymerase, or both the N-terminal and C-terminal regions of the polymerase. Where the polymerase includes an exogenous or heterologous feature at both the N-terminal and C-terminal regions, the exogenous or heterologous features can be the same (e.g., a polyhistidine tag, e.g., a His10 tag, at both the N- and C-terminal regions) or different (e.g., a biotin ligase recognition sequence at the N-terminal region and a polyhistidine tag, e.g., His10 tag, at the C-terminal region). Optionally, a terminal region (e.g., the N- or C-terminal region) of a polymerase of the invention can comprise two or more exogenous or heterologous features which can be the same or different (e.g., a biotin ligase recognition sequence and a polyhistidine tag at the N-terminal region, a biotin ligase recognition sequence, a polyhistidine tag, and a Factor Xa recognition site at the N-terminal region, and the like). As a few examples, the polymerase can include a polyhistidine tag at the C-terminal region, a biotin ligase recognition sequence and a polyhistidine tag at the N-terminal region, a biotin ligase recognition sequence and a polyhistidine tag at the N-terminal region and a polyhistidine tag at the C-terminal region, or a polyhistidine tag and a biotin ligase recognition sequence at the C-terminal region.

Making and Isolating Recombinant Polymerases

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase of the invention. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in the active site of polymerases, including for modifying steric features in or near the active site to permit improved access by nucleotide analogs are found hereinabove and, e.g., in PCT Publication Nos. WO 2007/076057 and WO 2008/051530.

Additional useful references for mutation, recombinant and in vitro nucleic acid manipulation methods (including cloning, expression, PCR, and the like) include Berger and Kimmel, Guide to Molecular Cloning Techniques, Methods in Enzymology volume 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley); Chen et al. (ed) PCR Cloning Protocols, Second Edition (Methods in Molecular Biology, volume 192) Humana Press; and in Viljoen et al. (2005) Molecular Diagnostic PCR Handbook Springer, ISBN 1402034032.

In addition, a plethora of kits are commercially available for the purification of plasmids or other relevant nucleic acids from cells, (see, e.g., EasyPrep™ FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla.

Nucleic acids encoding the recombinant polymerases of the invention are also a feature of the invention. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids of the invention are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2.sup.nd Edition Wiley-Liss, N.Y.; Walker (1996) The Protein Protocols Handbook Humana Press, N.J., Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3rd Edition Springer Verlag, N.Y.; Janson and Ryden (1998) Protein Purification: Principles, High Resolution Methods and Applications, Second Edition Wiley-VCH, N.Y.; and Walker (1998) Protein Protocols on CD-ROM Humana Press, N.J.; and the references cited therein. Additional details regarding protein purification and detection methods can be found in Satinder Ahuja ed., Handbook of Bioseparations, Academic Press (2000).

Nucleic Acid and Polypeptide Sequences and Variants

As described herein, the invention also features polynucleotide sequences encoding, e.g., a polymerase as described herein. Examples of polymerase sequences that include features found herein, e.g., as in Table 2 are provided. However, one of skill in the art will immediately appreciate that the invention is not limited to the specifically exemplified sequences. For example, one of skill will appreciate that the invention also provides, e.g., many related sequences with the functions described herein, e.g., polynucleotides and polypeptides encoding conservative variants of a polymerase of Table 2 and or any other specifically listed polymerase herein. Combinations of any of the mutations noted herein are also features of the invention.

Accordingly, the invention provides a variety of polypeptides (polymerases) and polynucleotides (nucleic acids that encode polymerases). Exemplary polynucleotides of the invention include, e.g., any polynucleotide that encodes a polymerase of Table 2 or otherwise described herein. Because of the degeneracy of the genetic code, many polynucleotides equivalently encode a given polymerase sequence. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention (e.g., that specifically recognizes a feature of the polymerase that confers decreased branching or increased complex stability.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant mutational feature (for example, the conservative substitution can be of a residue distal to the active site region, or distal to an interdomain stability region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 1

Conservative Amino Acid Substitutions

| Nonpolar and/or aliphatic side chains | Polar, uncharged side chains | Aromatic side chains | Positively charged side chains | Negatively charged side chains |
| --- | --- | --- | --- | --- |
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention. In addition, target nucleic acids which hybridize to a nucleic acid of the invention under high, ultra-high and ultra-ultra high stringency conditions, where the nucleic acids encode mutants corresponding to those noted in Tables 2 and 3 or other listed polymerases, are a feature of the invention. Examples of such nucleic acids include those with one or a few silent or conservative nucleic acid substitutions as compared to a given nucleic acid sequence encoding a polymerase of Table 2 (or other exemplified polymerase), where any conservative substitutions are for residues other than those noted in Table 2 or elsewhere as being relevant to a feature of interest (improved nucleotide analog incorporations, etc.).

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, N.Y.), as well as in Current Protocols in Molecular Biology, Ausubel et al., eds., Current Protocols, a joint venture between Greene Publishing Associates, Inc. and John Wiley & Sons, Inc., (supplemented through 2011); Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C. with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target "Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more identity, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2011).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

For reference, the amino acid sequence of a wild-type DPO4 polymerase is presented in Table 2.

Exemplary Mutation Combinations

A list of exemplary polymerase mutation combinations and the amino acid sequences of recombinant DPO4 polymerases harboring the exemplary mutation combinations are provided in Table 2. Positions of amino acid substitutions are identified relative to a wildtype DPO4 DNA polymerase (SEQ ID NO:1). Polymerases of the invention (including those provided in Table 2) can include any exogenous or heterologous feature (or combination of such features) at the N- and/or C-terminal region. For example, it will be understood that polymerase mutants in Table 2 that do not include, e.g., a C-terminal polyhistidine tag can be modified to include a polyhistidine tag at the C-terminal region, alone or in combination with any of the exogenous or heterologous features described herein. The variants set forth herein include a deletion of the last 12 amino acids of the protein (i.e., amino acids 341-352) so as to, e.g., increase protein solubility in bacterial expression systems.

TABLE 2

| DPO4 Variants Identified through Rational Design | |
|---|---|
| SEQ ID NO | Amino Acid Sequence |
| 1<br>wt DPO4 DNA polymerase | MIVLFVDFDYFYAQVEEVLNPSLKGKPVVVCVFSGRFEDSGAVA<br>TANYEARKFGVKAGIPIVEAKKILPNAVYLPMRKEVYQQVSSRI<br>MNLLREYSEKIEIASIDEAYLDISDKVRDYREAYNLGLEIKNKI<br>LEKEKITVTVGISKNKVFAKIAADMAKPNGIKVIDDEEVKRLIR<br>ELDIADVPGIGNITAEKLKKLGINKLVDTLSIEFDKLKGMIGEA<br>KAKYLISLARDEYNEPIRTRVRKSIGRIVTMKRNSRNLEEIKPY<br>LFRAIEESYYKLDKRIPKAIHVVAVTEDLDIVSRGRTFPHGISK<br>ETAYSESVKLLQKILEEDERKIRRIGVRFSKFIEAIGLDKFFDT |
| 2<br>C1816<br>A42V_K56Y_M76W_K78N_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_I295S_<br>V296Q_S297Y_G299W_<br>R300S_T301W_K317Q_<br>K321Q_E324K_E325K_<br>E327K Δ341-352 | MIVLFVDFDYFYAQVEEVLNPSLKGKPVVVCVFSGRFEDSGVVA<br>TANYEARKFGVYAGIPIVEAKKILPNAVYLPWRNLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 3<br>C3694<br>R36K_A42V_K56Y_M76W_<br>K78D_E79L_Q82W_Q83G_<br>S86E_K152L_I153T_A155G_<br>D156R_P184L_G187P_<br>N188Y_I189W_T190Y_I248T<br>K252Q_R253Q_V289W_<br>T290K_E291S_D292Y_<br>L293W_D294N_I295S_<br>V296Q_S297Y_G299W_<br>R300S_T301W_K317Q_<br>K321Q_E324K_E325K_<br>E327K Δ341-352 | MIVLFVDFDYFYAQVEEVLNPSLKGKPVVVCVFSGKFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMQQNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 4<br>C3405<br>A42V_K56Y_M76W_K78Q_<br>E79L_Q82W_Q83G_S86E_<br>K152L_I153T_A155G_<br>D156R_P184L_G187P_<br>N188Y_I189W_T190Y_<br>I248T_V289W_T290K_E291S_<br>D292Y_L293W_D294N_<br>I295S_V296Q_S297Y_G299W_<br>R300S_T301W_K317Q_ | MIVLFVDFDYFYAQVEEVLNPSLKGKPVVVCVFSGRFEDSGVVA<br>TANYEARKFGVYAGIPIVEAKKILPNAVYLPWRQLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |

TABLE 2-continued

DPO4 Variants Identified through Rational Design

| SEQ ID NO | Amino Acid Sequence |
|---|---|
| K321Q_E324K_E325K_<br>E327K Δ341-352 | |
| 5<br>C2615<br>C31S_A42V_K56Y_M76W_<br>K78D_E79L_Q82W_Q83G_<br>S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K Δ341-352 | MIVLFVDFDYFYAQVEEVLNPSLKGKPVVVSVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 6<br>C3413<br>A42V_K56Y_M76W_K78Q_<br>E79Y_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K Δ341-352 | MIVLFVDFDYFYAQVEEVLNPSLKGKPVVVCVFSGRFEDSGVVA<br>TANYEARKFGVYAGIPIVEAKKILPNAVYLPWRQYVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 7<br>C3416<br>A42V_K56Y_M76W_K78Q_<br>E79I_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_I295S_<br>V296Q_S297Y_G299W_<br>R300S_T301W_K317Q_<br>K321Q_E324K_E325K_<br>E327K Δ341-352 | MIVLFVDFDYFYAQVEEVLNPSLKGKPVVVCVFSGRFEDSGVVA<br>TANYEARKFGVYAGIPIVEAKKILPNAVYLPWRQIVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 8<br>C3410<br>A42V_K56Y_M76W_K78Q_<br>E79N_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K Δ341-352 | MIVLFVDFDYFYAQVEEVLNPSLKGKPVVVCVFSGRFEDSGVVA<br>TANYEARKFGVYAGIPIVEAKKILPNAVYLPWRQNVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 9<br>C3417<br>A42V_K56Y_M76W_K78Q_<br>E79M_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K Δ341-352 | MIVLFVDFDYFYAQVEEVLNPSLKGKPVVVCVFSGRFEDSGVVA<br>TANYEARKFGVYAGIPIVEAKKILPNAVYLPWRQMVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 10<br>C3687 | MIVLFVDFDYFYAQVEEVLNPSLKGKPVVVCVFSGRFEDSGVVA<br>TANYEARKFGVYAGIPIVEAKKILPNAVYLPWRDLVYWGVSERI |

TABLE 2-continued

DPO4 Variants Identified through Rational Design

| SEQ ID NO | Amino Acid Sequence |
|---|---|
| A42V_K56Y_M76W_K78D_ E79L_Q82W_Q83G_S86E_ K152L_I153T_A155G_ D156R_P184L_G187P_ N188Y_I189W_T190Y_I248T_ K252D_R253Q_V289W_ T290K_E291S_D292Y_ L293W_D294N_I295S_ V296Q_S297Y_G299W_ R300S_T301W_K317Q_ K321Q_E324K_ E325K_E327K Δ341-352 | MNLLREYSEKIEIASIDEAYLDISDKVRDYREAYNLGLEIKNKI LEKEKITVTVGISKNKVFALTAGRMAKPNGIKVIDDEEVKRLIR ELDIADVLGIPYWYAEKLKKLGINKLVDTLSIEFDKLKGMIGEA KAKYLISLARDEYNEPIRTRVRKSIGRTVTMDQNSRNLEEIKPY LFRAIEESYYKLDKRIPKAIHVVAWKSYWNSQYRWSWFPHGISK ETAYSESVQLLQQILKKDKRKIRRIGVRFSKF |
| 11 C3693 A42V_K56Y_M76W_K78D_ E79L_Q82W_Q83G_S86E_ K152L_I153T_A155G_ D156R_P184L_G187P_ N188Y_I189W_T190Y_I248T_ K252Q_R253Q_V289W_ T290K_E291S_D292Y_ L293W_D294N_I295S_ V296Q_S297Y_G299W_ R300S_T301W_K317Q_ K321Q_E324K_E325K_ E327K Δ341-352 | MIVLFVDFDYFYAQVEEVLNPSLKGKPVVVCVFSGRFEDSGVVA TANYEARKFGVYAGIPIVEAKKILPNAVYLPWRDLVYWGVSERI MNLLREYSEKIEIASIDEAYLDISDKVRDYREAYNLGLEIKNKI LEKEKITVTVGISKNKVFALTAGRMAKPNGIKVIDDEEVKRLIR ELDIADVLGIPYWYAEKLKKLGINKLVDTLSIEFDKLKGMIGEA KAKYLISLARDEYNEPIRTRVRKSIGRTVTMQQNSRNLEEIKPY LFRAIEESYYKLDKRIPKAIHVVAWKSYWNSQYRWSWFPHGISK ETAYSESVQLLQQILKKDKRKIRRIGVRFSKF |
| 12 C3407 A42V_K56Y_M76W_K78D_ E79L_Q82W_Q83G_S86E_ K152L_I153T_A155G_ D156R_P184L_G187P_ N188Y_I189W_T190Y_I248T_ K252R_V289W_T290K_ E291S_D292Y_L293W_ D294N_I295S_V296Q_ S297Y_G299W_R300S_ T301W_K317Q_K321Q_ E324K_E325K_E327K Δ341-352 | MIVLFVDFDYFYAQVEEVLNPSLKGKPVVVCVFSGRFEDSGVVA TANYEARKFGVYAGIPIVEAKKILPNAVYLPWRDLVYWGVSERI MNLLREYSEKIEIASIDEAYLDISDKVRDYREAYNLGLEIKNKI LEKEKITVTVGISKNKVFALTAGRMAKPNGIKVIDDEEVKRLIR ELDIADVLGIPYWYAEKLKKLGINKLVDTLSIEFDKLKGMIGEA KAKYLISLARDEYNEPIRTRVRKSIGRTVTMRRNSRNLEEIKPY LFRAIEESYYKLDKRIPKAIHVVAWKSYWNSQYRWSWFPHGISK ETAYSESVQLLQQILKKDKRKIRRIGVRFSKF |
| 13 C3585 A42V_K56Y_M76W_K78D_ E79L_Q82W_Q83G_S86E_ K152L_I153T_A155G_ D156R_P184L_G187P_ N188Y_I189W_T190Y_I248T_ N254E_V289W_T290K_ E291S_D292Y_L293W_ D294N_I295S_V296Q_ S297Y_G299W_R300S_ T301W_K317Q_K321Q_ E324K_E325K_E327K Δ341-352 | MIVLFVDFDYFYAQVEEVLNPSLKGKPVVVCVFSGRFEDSGVVA TANYEARKFGVYAGIPIVEAKKILPNAVYLPWRDLVYWGVSERI MNLLREYSEKIEIASIDEAYLDISDKVRDYREAYNLGLEIKNKI LEKEKITVTVGISKNKVFALTAGRMAKPNGIKVIDDEEVKRLIR ELDIADVLGIPYWYAEKLKKLGINKLVDTLSIEFDKLKGMIGEA KAKYLISLARDEYNEPIRTRVRKSIGRTVTMKRKSRNLEEIKPY LFRAIEESYYKLDKRIPKAIHVVAWKSYWNSQYRWSWFPHGISK ETAYSESVQLLQQILKKDKRKIRRIGVRFSKF |
| 14 C3593 A42V_K56Y_M76W_K78D_ E79L_Q82W_Q83G_S86E_ K152L_I153T_A155G_ D156R_P184L_G187P_ N188Y_I189W_T190Y_I248T_ V289W_T290K_E291S_ D292Y_L293W_D294N_ I295S_V296Q_S297Y_ G299W_R300S_T301W_ K317Q_K321Q_E324K_ E325K_E327K_R331D Δ341-352 | MIVLFVDFDYFYAQVEEVLNPSLKGKPVVVCVFSGRFEDSGVVA TANYEARKFGVYAGIPIVEAKKILPNAVYLPWRDLVYWGVSERI MNLLREYSEKIEIASIDEAYLDISDKVRDYREAYNLGLEIKNKI LEKEKITVTVGISKNKVFALTAGRMAKPNGIKVIDDEEVKRLIR ELDIADVLGIPYWYAEKLKKLGINKLVDTLSIEFDKLKGMIGEA KAKYLISLARDEYNEPIRTRVRKSIGRTVTMKRNSRNLEEIKPY LFRAIEESYYKLDKRIPKAIHVVAWKSYWNSQYRWSWFPHGISK ETAYSESVQLLQQILKKDKRKIDRIGVRFSKF |
| 15 C3594 A42V_K56Y_M76W_K78D_ | MIVLFVDFDYFYAQVEEVLNPSLKGKPVVVCVFSGRFEDSGVVA TANYEARKFGVYAGIPIVEAKKILPNAVYLPWRDLVYWGVSERI MNLLREYSEKIEIASIDEAYLDISDKVRDYREAYNLGLEIKNKI |

TABLE 2-continued

DPO4 Variants Identified through Rational Design

| SEQ ID NO | Amino Acid Sequence |
|---|---|
| E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_R331E<br>Δ341-352 | LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIERIGVRFSKF |
| 16<br>C3591<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_R331N<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKINRIGVRFSKF |
| 17<br>C3596<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_R331L<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKILRIGVRFSKF |
| 18<br>C3598<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_R332K<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRKIGVRFSKF |
| 19<br>C3604<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_R332A<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRAIGVRFSKF |
| 20<br>C3600<br>A42V_K56Y_M76W_K78D_<br>E79L_Q82W_Q83G_S86E_ | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR |

TABLE 2-continued

DPO4 Variants Identified through Rational Design

| SEQ ID NO | Amino Acid Sequence |
|---|---|
| K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_R332Q<br>Δ341-352 | ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRQIGVRFSKF |
| 21<br>C3601<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_R332S<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRSIGVRFSKF |
| 22<br>C3605<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_G334N<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRINVRFSKF |
| 23<br>C3606<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_G334Q<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIQVRFSKF |
| 24<br>C3609<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_G334F<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIFVRFSKF |
| 25<br>C3610<br>A42V_K56Y_M76W_K78D_<br>E79L_Q82W_Q83G_S86E_<br>K152L_I153T_A155G_ | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA |

TABLE 2-continued

DPO4 Variants Identified through Rational Design

| SEQ ID NO | Amino Acid Sequence |
|---|---|
| D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_G334A<br>Δ341-352 | KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIAVRFSKF |
| 26<br>C3618<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_S338Y<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFYKF |
| 27<br>C3619<br>A42V_K56Y_M76W_K78D_<br>E79L_Q82W_Q83G_S86E_<br>K152L_I153T_A155G_<br>D156R_P184L_G187P_<br>N188Y_I189W_T190Y_I248T_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K_S338F<br>Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFALTAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFFKF |
| 28<br>C3488<br>A42V_K56Y_M76W_K78D_<br>E79L_Q82W_Q83G_S86E_<br>K152A_I153V_A155G_<br>D156R_P184L_G187P_<br>N188Y_I189W_T190Y_I248T_<br>V289W_T290K_E291S_<br>D292Y_L293W_D294N_I295S_<br>V296Q_S297Y_G299W_<br>R300S_T301W_K317Q_<br>K321Q_E324K_E325K_<br>E327K_Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFAAVAGRMAKPNGIKVIDDEEVKRLIR<br>ELDIADVLGIPYWYAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 29<br>C4552<br>A42V_K56Y_M76W_K78D_<br>E79L_Q82W_Q83G_S86E_<br>K152A_1153V_A155G_<br>D156R_P184L_G187P_<br>N188Y_I189Q_I248T_<br>V289W_T290K_E291S_<br>D292Y_L293W_D294N_I295S_<br>V296Q_S297Y_G299W_<br>R300S_T301W_K317Q_<br>K321Q_E324K_E325K_<br>E327K_Δ341-352 | MIVLFVDFDYFYAQVEEVLNPSLKGKPVVVCVFSGRFEDSGVVA<br>TANYEARKFGVYAGIPIVEAKKILPNAVYLPWRDLVYWGVSERI<br>MNLLREYSEKIEIASIDEAYLDISDKVRDYREAYNLGLEIKNKI<br>LEKEKITVTVGISKNKVFAAVAGRMAKPNGIKVIDDEEVKRLIR<br>ELDIADVQGIPYFTAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 30<br>C4760<br>A42V_K56Y_E63R_<br>M76W_K78D_E79L_Q82W_<br>Q83G_S86E_K152A_I153V_<br>A155G_D156R_P184Q_<br>G187P_N188Y_I189F_<br>I248T_V289W_T290K_ | MIVLFVDFDYFYAQVEEVLNPSLKGKPVVVCVFSGRFEDSGVVA<br>TANYEARKFGVYAGIPIVRAKKILPNAVYLPWRDLVYWGVSERI<br>MNLLREYSEKIEIASIDEAYLDISDKVRDYREAYNLGLEIKNKI<br>LEKEKITVTVGISKNKVFAAVAGRMAKPNGIKVIDDEEVKRLIR<br>ELDIADVQGIPYFTAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |

TABLE 2-continued

DPO4 Variants Identified through Rational Design

| SEQ ID NO | Amino Acid Sequence |
|---|---|
| E291S_D292Y_L293W_<br>D294N_I295S_V296Q_<br>S297Y_G299W_R300S_<br>T301W_K317Q_K321Q_<br>E324K_E325K_E327K<br>Δ341-352 | |
| 31<br>C4842<br>A42V_K56Y_E63R_M76W_<br>K78D_E79L_Q82W_Q83G_<br>S86E_K152A_I153V_<br>A155G_D156R_P184Q_<br>G187P_N188Y_I189F_<br>K243R_I248T_V289W_<br>T290K_E291S_D292Y_<br>L293W_D294N_I295S_<br>V296Q_S297Y_G299W_<br>R300S_T301W_<br>K317Q_K321Q_E324K_<br>E325K_E327K Δ341-352 | MIVLFVDFDYFYAQVEEVLNPSLKGKPVVVCVFSGRFEDSGVVA<br>TANYEARKFGVYAGIPIVRAKKILPNAVYLPWRDLVYWGVSERI<br>MNLLREYSEKIEIASIDEAYLDISDKVRDYREAYNLGLEIKNKI<br>LEKEKITVTVGISKNKVFAAVAGRMAKPNGIKVIDDEEVKRLIR<br>ELDIADVQGIPYFTAEKLKKLGINKLVDTLSIEFDKLKGMIGEA<br>KAKYLISLARDEYNEPIRTRVRRSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 32<br>C4852<br>A42V_K56Y_E63R_M76W_<br>K78D_E63R_E79L_Q82W_<br>Q83G_S86E_K152A_I153V_<br>A155G_D156R_P184Q_<br>G187P_N188Y_I189F_<br>I248T_N254D_<br>T290K_E291S_D292Y_<br>L293W_D294N_I295S_<br>V296Q_S297Y_G299W_<br>R300S_T301W_K317Q_<br>K321Q_E324K_E325K_<br>E327K Δ341-352 | MIVLFVDFDYFYAQVEEVLNPSLKGKPVVVCVFSGRFEDSGVVA<br>TANYEARKFGVYAGIPIVRAKKILPNAVYLPWRDLVYWGVSERI<br>MNLLREYSEKIEIASIDEAYLDISDKVRDYREAYNLGLEIKNKI<br>LEKEKITVTVGISKNKVFAAVAGRMAKPNGIKVIDDEEVKRLIR<br>ELDIADVQGIPYFTAEKLKKLGINKLVDTLSIEFDKLKGMIGEA<br>KAKYLISLARDEYNEPIRTRVRKSIGRTVTMKRDSRNLEEIKPY<br>LFRAIEESYYKLDKRIPKAIHVVAWKSYWNSQYRWSWFPHGISK<br>V289WETAYSESVQLLQQILKKDKRKIRRIGVRFSKF |
| 33<br>C4862<br>A42V_K56Y_V62K_E63R_<br>M76W_K78D_E79L_Q82W_<br>Q83G_S86E_K152A_I153V_<br>A155G_D156R_P184Q_<br>G187P_N188Y_1189F_<br>I248T_V289W_T290K_<br>E291S_D292Y_L293W_<br>D294N_I295S_V296Q_<br>S297Y_G299W_R300S_<br>T301W_K317Q_K321Q_<br>E324K_E325K_E327K<br>Δ341-352 | MIVLFVDFDYFYAQVEEVLNPSLKGKPVVVCVFSGRFEDSGVVA<br>TANYEARKFGVYAGIPIKRAKKILPNAVYLPWRDLVYWGVSERI<br>MNLLREYSEKIEIASIDEAYLDISDKVRDYREAYNLGLEIKNKI<br>LEKEKITVTVGISKNKVFAAVAGRMAKPNGIKVIDDEEVKRLIR<br>ELDIADVQGIPYFTAEKLKKLGINKLVDTLSIEFDKLKGMIGEA<br>KAKYLISLARDEYNEPIRTRVRKSIGRTVTMKRNSRNLEEIKPY<br>LFRAIEESYYKLDKRIPKAIHVVAWKSYWNSQYRWSWFPHGISK<br>ETAYSESVQLLQQILKKDKRKIRRIGVRFSKF |
| 34<br>C4907<br>A42V_K56Y_E63R_M76W_<br>K78D_E79L_Q82W_Q83G_<br>S86E_K152A_I153V_<br>A155G_D156R_P184Q_<br>G187P_N188Y_I189F_<br>K243R_I248T_N254D_<br>V289W_T290K_E291S_<br>D292Y_L293W_D294N_<br>I295S_V296Q_S297Y_<br>G299W_R300S_T301W_<br>K317Q_K321Q_E324K_<br>E325K_E327K Δ341-352 | MIVLFVDFDYFYAQVEEVLNPSLKGKPVVVCVFSGRFEDSGVVA<br>TANYEARKFGVYAGIPIVRAKKILPNAVYLPWRDLVYWGVSERI<br>MNLLREYSEKIEIASIDEAYLDISDKVRDYREAYNLGLEIKNKI<br>LEKEKITVTVGISKNKVFAAVAGRMAKPNGIKVIDDEEVKRLIR<br>ELDIADVQGIPYFTAEKLKKLGINKLVDTLSIEFDKLKGMIGEA<br>KAKYLISLARDEYNEPIRTRVRRSIGRTVTMKRDSRNLEEIKPY<br>LFRAIEESYYKLDKRIPKAIHVVAWKSYWNSQYRWSWFPHGISK<br>ETAYSESVQLLQQILKKDKRKIRRIGVRFSKF |

The Examples and polymerase variants provided below further illustrate and exemplify the compositions of the present invention and methods of preparing and using such compositions. It is to be understood that the scope of the present invention is not limited in any way by the scope of the following Examples.

EXAMPLES

Example 1

Identification of DPO4 as a Candidate Translesion DNA Polymerase for Incorporation of Bulky Nucleotide Analogs During Template-Mediated DNA Synthesis To identify a DNA polymerase with the ability to synthesize daughter strands using "bulky" substrates (i.e., able to bind and incorporate heavily substituted nucleotide analogs into a growing nucleic acid strand), a screen was conducted of several commercially available polymerases. Candidate polymerases were assessed for the ability to extend an oligonucleotide-bound primer using a pool of dNTP analogs substituted with alkyne linkers on both the backbone α-phosphate and the nucleobase moieties (i.e., model bulky substrates, referred to herein generally as, "dNTP-2c"). Polymerases screened for activity included the following: Vent$_R$ (Exo-), Deep Vent$_R$® (Exo-), Therminator, Therminator II, Therminator III, Therminator Y, 9° N$_m$, PWO, PWO SuperYield, PyroPhage 3173 (Exo-), Bst, Large Fragment, Exo-Pfu, Platinum Genotype TSP, Hemo Klen Taq, Taq, MasterAMP Taq, Phi29, Bsu, Large Fragment, Exo-Minus Klenow (D355A, E357A), Sequenase Version 2.0, Transcriptor, Maxima, Thermoscript, M-MuLV (RNase H—), AMV, M-MuLV, Monsterscript, and DPO4. Of the polymerases tested, DPO4 (naturally expressed by the archaea, *Sulfolobus solfataricus*) was most able to effectively extend a template-bound primer with dNTP-2c nucleotide analogs. Without being bound by theory, it was speculated that DPO4, and possibly other members of the translesion DNA polymerase family (i.e., class Y DNA polymerases), may be able to effectively utilize bulky nucleotide analogs as substrates owing to their relatively large substrate binding sites, which have evolved to accommodate naturally occurring, bulky DNA lesions.

Example 2

Identification of "Hot Spots" for Directed Mutagenesis in the DPO4 Protein and Screen of DPO4 Mutant Libraries to Identify Optimized Sequence Motifs As an initial step in generating DPO4 variants with improved polymerase activity in the presence of non-natural substrates, the "HotSpot Wizard" web tool was used to identify amino acids in the DPO4 protein to target for mutagenesis. This tool implements a protein engineering protocol that targets evolutionarily variable amino acid positions located in, e.g., the enzyme active site. "Hot spots" for mutation are selected through the integration of structural, functional, and evolutionary information (see, e.g., Pavelka et al., "HotSpot Wizard: a Web Server for Identification of Hot Spots in Protein Engineering" (2009) Nuc Acids Res 37 doi:10.1093/nar/gkp410). Applying this tool to the DPO4 protein, it was observed that hot spot residues identified tended to cluster into certain zones, or regions, spread throughout the full amino acid sequence. Arbitrary boundaries were set to distinguish 15 such regions, designated "Mut1"-"Mut15", in which mutagenesis hot spots are concentrated. These 15 "Mut" regions are illustrated in FIG. 1 with hot spot residues identified by underscoring.

To screen for DPO4 variants with improved polymerase activity based on hot spot mapping, saturation mutagenesis libraries were created for the Mut regions, in which hot spot amino acids were changed, while conserved amino acids were left unaltered. Screening was conducted using a 96-well plate platform, and polymerase activity was assessed with a primer extension assay using "dNTP-OAc" nucleotide analogs as substrates. These model bulky substrates are substituted with triazole acetate moieties conjugated to alkyne substituents on both the α-phosphate and the nucleobase moieties. Screening results identified two Mut regions in particular that consistently produced DPO4 mutants with enhanced activity. These regions, "Mut_4" and "Mut_11", correspond to amino acids 76-86 and amino acids 289-304, respectively, of the DPO4 protein.

Example 3

Semi-Rational Approaches to Designing DPO4 Variants with Enhanced Polymerization Activity To continue evolving DPO4 variants with improved utilization of bulky substrates, "semi-rational" design approaches were taken following a number of different strategies. In one strategy, disclosed in Applicants' co-pending PCT patent application no. PCT/US2018/030972, herein incorporated by reference in its entirety, a library was created that directed random mutagenesis on positions 152, 153, 155, and 156 (corresponding to the Mut_6 region) on the previously identified high performing variant, C0534 (disclosed in applicants' co-pending PCT patent application no. PCT/US2016/061661, herein incorporated by reference in its entirety). Screening of this library was conducted as described above and results identified three variants in particular that demonstrated superior primer extension activity using bulky nucleotide analog substrates. These variants are the previously disclosed C1065, C1066, and C1067.

In yet other strategies, high-performing variants, including C0416 and C0534 (disclosed in applicants' co-pending PCT application no. PCT/US2016/061661) and C1066, C01067, C1454, and C1187 were subject to random or directed mutagenesis as disclosed herein to create libraries for further screening. Screening of these libraries was conducted as described above and results identified several variants that performed at least as well as the parental variants in primer extension assays using bulky XNTP substrates. One in particular, C1816 (SEQ ID NO:2), displayed robust primer extension activity and was selected as a scaffold for further rational protein design.

Example 4

Accuracy Assessment of DPO4 Polymerase Variants Via Sequencing by Expansion (SBX)

This Example describes a strategy to evaluate the accuracy of DPO4 variant polymerase activity by determining the sequence of primer extension products (e.g., "Xpandomers") using a nanopore-based single molecule sequencing system. (e.g., "sequencing by expansion" (SBX) as disclosed in Applicants' issued U.S. Pat. No. 7,939,259, "High Throughput Nucleic Acid Sequencing by Expansion", herein incorporated by reference in its entirety). Briefly, an exemplary SBX protocol includes the following steps: first, a primer extension reaction is conducted in which the polymerase transcribes the sequence of the template strand using highly engineered, expandable nucleoside triphosphates (i.e., XNTPs) into a highly measurable surrogate polymer (i.e., an Xpandomer). The Xpandomer encodes sequence information in high signal-to-noise reporters that are unique to each of the four XNTPs. Xpandomers may be synthesized in a solution containing 54, of "buffer A" (40 mM TrisOAc, pH 8.32, 400 mM NH$_4$OAc, pH 6.88 and 40% PEG8K) and 1 µL "sample B1" (2.2 pmol of single-stranded DNA template, 2.0 pmol of extension oligonucleotide, and 0.6 µg purified polymerase protein). The extension oligonucleotide is designed to include features that promote membrane localization and translocation control of extension products through the nanopore (see, e.g., Applicants' co-pending U.S. published patent application no. 2017/0073740, "Translocation Control for Sensing by a Nanopore", herein incorporated by reference in its entirety). An XNTP substrate sample is prepared that contains 1 nmol each of XATP, XCTP, XGTP, and XTTP (structural details of XNTPs are disclosed, in Applicants' issued patents and pending patent applications, e.g., U.S. published patent application no. 2016/0145292, "Phosphoramidate Esters and Use and Synthesis thereof", herein incorporated by reference in its entirety) and 14, of this is added to 34, of "sample B2" (16.66% DMF, 333.3304 polyphosphate 60, and 1.66 mM MnCl$_2$). Extension reactions are run by mixing 64, of (samples A+B1) with 44, of (XNTPs+sample B2) followed by incubation at 37° C. for 20 minutes.

Secondly, the phosphoramidate bonds in the backbone of the newly synthesized Xpandomers are cleaved to linearize the polymers. To accomplish this, Xpandomers are processed by adding 74, "solution Q1" (100 mM EDTA, 2 mM THPTA, 2% Tween-20) to 104, of the extension reaction and incubating 2 minutes at 85° C. Amine modification is then performed by adding 34, of NaHCO$_3$, pH 9 and 104, 1M succinic anhydride in DMF and incubating at 70° C. for 3 minutes. Cleavage of the phosphoramidate bonds is then carried out by adding 504, of 37% HCl and incubating at 55° C. for 5 minutes. Cleaved Xpandomer products are then purified by loading the sample onto a QIAquick column (QIAGEN), centrifuging for 2 minutes, washing twice with 3004, "solution W1" (2M GuCl, 10 mM IVIES, pH5, 1 mM EDTA), and washing once with 3004, 100% DMF. The column is then transferred to a fresh tube containing 1004, "solution H1" (3M NH$_4$Cl, 0.5M GuCl, 10% DMSO, 10 mM sodium hexanoate, 10 mM HEPES, pH 7.4) and 2 nmol of "duplex interrupter" oligonucleotide. 504, "solution El" (30% ACN, 1% DMSO, 0.1 mM EDTA) is added and samples are incubated for 2 minutes followed by centrifugation to collect purified Xpandomer.

Next, the sequences of the linearized Xpandomers are determined by read-out of the reporter moieties using a wild-type alpha-hemolysin nanopore system. A DPhPE/hexadecane bilayer is initially prepared in "buffer B 1" (2M NH$_4$Cl, 100 mM HEPES, pH 7.4) then an alpha-hemolysin nanopore is inserted into the bilayer, and the cis well is perfused with "buffer B2" (0.4M NH$_4$Cl, 0.6M GuCl, 100 mM HEPES, pH 7.4). The Xpandomer sample is prepared by heating to 70° C. for 2 minutes followed by cooling. 24, of sample is added to the cis well while mixing. A pulse voltage of 90 mV/390 mV/10 µs is then applied to drive the single molecule Xpandomer through the nanopore and sequence data is acquired by Labview software.

Example 5

Design of DPO4 Variants with Improved Accuracy

During the course of evaluating the accuracy of thousands of DPO4 variants with the SBX methodology, certain repeated patterns of nucleotide incorporation errors were observed. Such patterns appeared to reflect template-dependent effects. For example, one pattern repeatedly noted was polymerase misincorporation at a dinucleotide repeat motif in the template. Without be being bound by theory, it was speculated that such repeat motifs may trigger replication slippage, during which the daughter strand and the polymerase disengage from the replication fork, followed by resumption of replication upon misalignment of the daughter strand to the template. Efforts were therefore undertaken to engineer DPO4 variants with improved accuracy during replication of templates with challenging sequence motifs. This endeavor involved a rational approach to protein design in which the crystal structure of DPO4 was relied upon to identify regions of the protein predicted to influence substrate and/or cofactor binding in the active site of the enzyme. Specific residues targeted for mutation based on their position in the 3D structure of the DPO4 protein included amino acid positions 31, 36, 62, 63, 78, 79, 243, 252, 253, 254, 331, 332, 334, and 338. One mutation in particular, K78D, consistently improved replication accuracy when introduced, for example, into the C1816 variant backbone (SEQ ID NO:2). Interestingly, amino acid position 78 resides in an alpha helix that lies proximal to a conserved region that participates in coordinating Mg' in the polymerase active site. After evaluation of an extensive collection of novel DPO4 variants with amino acid substitutions at various combinations of the positions set forth above, the following substitutions were found to significantly improve polymerase accuracy and/or extension activity: C31S, R36K, V62K, E63R, E79L, E79D, E79I, K243R, K252D, K252Q, K252R, R253Q, N254K, N254D, R331D, R331E, R331N, R331L, R332K, R332A, R332Q, R332S, G334N, G334Q, G334F, G334A, S338Y, and S338F. Exemplary DPO4 variant sequences are set forth in Table 2 as SEQ ID NOs: 3-34.

All of the U.S. patents, U.S. patent application publications, U.S. patent applications, foreign patents, foreign patent applications and non-patent publications referred to in this specification and/or listed in the Application Data Sheet, including but not limited to U.S. Pat. No. 7,939,259, PCT Publication No. WO 2016/081871, U.S. Provisional Patent Application No. 62/597,109 and U.S. Provisional Patent Application No. 62/656,696, are incorporated herein by reference, in their entirety. Such documents may be incorporated by reference for the purpose of describing and disclosing, for example, materials and methodologies described in the publications, which might be used in connection with the presently described invention.

The invention claimed is:

1. An isolated recombinant DNA polymerase, which recombinant DNA polymerase comprises an amino acid sequence that is at least 90% identical to amino acids 1-340 of SEQ ID NO:1, which recombinant polymerase comprises a mutation at amino acid positions 63, 76, 78, 79, 82, 83, 86, 254, and 289, wherein the mutation at amino acid position 63 is E63R, the mutation at amino acid position 76 is M76W, the mutation at amino acid position 78 is K78D, the mutation at amino acid position 79 is E79L, the mutation at amino acid position 82 is Q82W, the mutation at amino acid position 86 is S86E, the mutation at amino acid position 254 is N254K or N254D, and the mutation at amino acid position 289 is V289W wherein identification of positions is relative to wildtype DPO4 polymerase (SEQ ID NO:1), and which recombinant DNA polymerase exhibits polymerase activity.

2. The polymerases of claim 1, further comprising at least one mutation at an amino acid position selected from the group consisting of 42, 56, 152, 153, 155, 156, 184, 187, 188, 189, 190, 248, 290, 291, 292, 293, 294, 295, 296, 297, 299, 300, 301, 317, 321, 324, 325, and 327.

3. The polymerase of claim 2, wherein the mutations at amino acid positions 42, 56, 152, 153, 155, 156, 184, 187, 188, 189, 190, 248, 290, 291, 292, 293, 294, 295, 296, 297, 299, 300, 301, 317, 321, 324, 325, and 327 are A42V, K56Y, K152L or K152A, I153T or I153V, A155G, D156R, P184L or P184Q, G187P, N188Y, I189W or I189F, T190Y, I248T, T290K, E291S, D292Y, L293W, D294N, I295S, V296Q, S297Y, G299W, R300S, T301W, K317Q, K321Q, E324K, E325K, and E327K.

4. A composition comprising a recombinant DNA polymerase as set forth in claim 1.

5. The composition of claim 4, wherein the composition is present in a DNA sequencing system that comprises at least one non-natural nucleotide analog substrate.

6. The polymerase of claim 1, wherein amino acids 341-352 relative to wildtype DPO4 polymerase (SEQ ID NO: 1) are deleted.

* * * * *

SEQUENCE LISTING

<160> NUMBER OF SEQ ID NOS: 34

<210> SEQ ID NO 1
<211> LENGTH: 352
<212> TYPE: PRT
<213> ORGANISM: Sulfolobus solfataricus

<400> SEQUENCE: 1

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Ala Val Ala Thr Ala Asn Tyr
        35                  40                  45

Glu Ala Arg Lys Phe Gly Val Lys Ala Gly Ile Pro Ile Val Glu Ala
    50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Val Thr Glu Asp Leu Asp Ile Val Ser Arg Gly Arg Thr Phe Pro His
    290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 2
<211> LENGTH: 340

```
<212> TYPE: PRT
<213> ORGANISM: Artificial sequence
<220> FEATURE:
<223> OTHER INFORMATION: DPO4 Variant

<400> SEQUENCE: 2

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asn Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 3
<211> LENGTH: 340
<212> TYPE: PRT
<213> ORGANISM: Artificial sequence
<220> FEATURE:
```

<223> OTHER INFORMATION: DPO4 Variant

<400> SEQUENCE: 3

```
Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Cys Val
            20                  25                  30

Phe Ser Gly Lys Phe Glu Asp Ser Gly Val Val Ala Thr Ala Asn Tyr
            35                  40                  45

Glu Ala Arg Lys Phe Gly Val Tyr Ala Gly Ile Pro Ile Val Glu Ala
        50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
        210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Gln Gln Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340
```

<210> SEQ ID NO 4
<211> LENGTH: 340
<212> TYPE: PRT
<213> ORGANISM: Artificial sequence
<220> FEATURE:
<223> OTHER INFORMATION: DPO4 Variant

<400> SEQUENCE: 4

```
Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Gln Leu Val
65                  70                  75                  80

Tyr Trp Gly Val Ser Glu Arg Ile Met Asn Leu Leu Arg Glu Tyr Ser
            85                  90                  95

Glu Lys Ile Glu Ile Ala Ser Ile Asp Glu Ala Tyr Leu Asp Ile Ser
        100                 105                 110

Asp Lys Val Arg Asp Tyr Arg Glu Ala Tyr Asn Leu Gly Leu Glu Ile
    115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
            165                 170                 175

Glu Leu Asp Ile Ala Asp Val Leu Gly Ile Pro Tyr Trp Tyr Ala Glu
        180                 185                 190

Lys Leu Lys Lys Leu Gly Ile Asn Lys Leu Val Asp Thr Leu Ser Ile
    195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
            245                 250                 255

Asn Leu Glu Glu Ile Lys Pro Tyr Leu Phe Arg Ala Ile Glu Glu Ser
        260                 265                 270

Tyr Tyr Lys Leu Asp Lys Arg Ile Pro Lys Ala Ile His Val Val Ala
    275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
            325                 330                 335

Phe Ser Lys Phe
        340
```

<210> SEQ ID NO 5
<211> LENGTH: 340
<212> TYPE: PRT
<213> ORGANISM: Artificial sequence
<220> FEATURE:
<223> OTHER INFORMATION: DPO4 Variant

<400> SEQUENCE: 5

```
Met Ile Val Leu Phe Val Asp Phe Asp Tyr Phe Tyr Ala Gln Val Glu
1               5                   10                  15
```

Glu Val Leu Asn Pro Ser Leu Lys Gly Lys Pro Val Val Ser Val
                20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Glu Ala
        50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Arg Glu Tyr Ser
                85                  90                  95

Glu Lys Ile Glu Ile Ala Ser Ile Asp Glu Ala Tyr Leu Asp Ile Ser
                100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Ile Gly Val Arg
                325                 330                 335

Phe Ser Lys Phe
            340

<210> SEQ ID NO 6
<211> LENGTH: 340
<212> TYPE: PRT
<213> ORGANISM: Artificial sequence
<220> FEATURE:
<223> OTHER INFORMATION: DPO4 Variant

<400> SEQUENCE: 6

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

-continued

```
Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Glu Ala
 50                  55                  60

Lys Lys Ile Leu Pro Asn Ala Val Tyr Leu Pro Trp Arg Gln Tyr Val
 65                  70                  75                  80

Tyr Trp Gly Val Ser Glu Arg Ile Met Asn Leu Leu Arg Glu Tyr Ser
                 85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
            290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340
```

<210> SEQ ID NO 7
<211> LENGTH: 340
<212> TYPE: PRT
<213> ORGANISM: Artificial sequence
<220> FEATURE:
<223> OTHER INFORMATION: DPO4 Variant

<400> SEQUENCE: 7

```
Met Ile Val Leu Phe Val Asp Phe Asp Tyr Phe Tyr Ala Gln Val Glu
 1               5                  10                  15

Glu Val Leu Asn Pro Ser Leu Lys Gly Lys Pro Val Val Val Cys Val
                 20                  25                  30

Phe Ser Gly Arg Phe Glu Asp Ser Gly Val Val Ala Thr Ala Asn Tyr
            35                  40                  45
```

Glu Ala Arg Lys Phe Gly Val Tyr Ala Gly Ile Pro Ile Val Glu Ala
            50                  55                  60

Lys Lys Ile Leu Pro Asn Ala Val Tyr Leu Pro Trp Arg Gln Ile Val
 65                  70                  75                  80

Tyr Trp Gly Val Ser Glu Arg Ile Met Asn Leu Leu Arg Glu Tyr Ser
                    85                  90                  95

Glu Lys Ile Glu Ile Ala Ser Ile Asp Glu Ala Tyr Leu Asp Ile Ser
                100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
        210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 8
<211> LENGTH: 340
<212> TYPE: PRT
<213> ORGANISM: Artificial sequence
<220> FEATURE:
<223> OTHER INFORMATION: DPO4 Variant

<400> SEQUENCE: 8

Met Ile Val Leu Phe Val Asp Phe Asp Tyr Phe Tyr Ala Gln Val Glu
 1               5                  10                  15

Glu Val Leu Asn Pro Ser Leu Lys Gly Lys Pro Val Val Val Cys Val
                20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Glu Ala
            50                  55                  60

Lys Lys Ile Leu Pro Asn Ala Val Tyr Leu Pro Trp Arg Gln Asn Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 9
<211> LENGTH: 340
<212> TYPE: PRT
<213> ORGANISM: Artificial sequence
<220> FEATURE:
<223> OTHER INFORMATION: DPO4 Variant

<400> SEQUENCE: 9

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Gln Met Val
65                  70                  75                  80

```
Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 10
<211> LENGTH: 340
<212> TYPE: PRT
<213> ORGANISM: Artificial Sequence
<220> FEATURE:
<223> OTHER INFORMATION: DPO4 Variant

<400> SEQUENCE: 10

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95
```

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Asp Gln Asn Ser Arg
            245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
            290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 11
<211> LENGTH: 340
<212> TYPE: PRT
<213> ORGANISM: Artificial sequence
<220> FEATURE:
<223> OTHER INFORMATION: DPO4 Variant

<400> SEQUENCE: 11

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
            85                  90                  95

Glu Lys Ile Glu Ile Ala Ser Ile Asp Glu Ala Tyr Leu Asp Ile Ser
            100                 105                 110

```
Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
        210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Gln Gln Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
        290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 12
<211> LENGTH: 340
<212> TYPE: PRT
<213> ORGANISM: Artificial sequence
<220> FEATURE:
<223> OTHER INFORMATION: DPO4 Variant

<400> SEQUENCE: 12

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125
```

```
Lys Asn Lys Ile Leu Glu Lys Glu Lys Ile Thr Val Thr Val Gly Ile
            130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Arg Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 13
<211> LENGTH: 340
<212> TYPE: PRT
<213> ORGANISM: Artificial sequence
<220> FEATURE:
<223> OTHER INFORMATION: DPO4 Variant

<400> SEQUENCE: 13

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
            130                 135                 140
```

```
Ser Lys Asn Lys Val Phe Ala Leu Thr Ala Gly Arg Met Ala Lys Pro
145                 150                 155                 160

Asn Gly Ile Lys Val Ile Asp Asp Glu Val Lys Arg Leu Ile Arg
            165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Pro Ile Arg Thr Arg
225                 230                 235                 240

Val Arg Lys Ser Ile Gly Arg Thr Val Thr Met Lys Arg Lys Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 14
<211> LENGTH: 340
<212> TYPE: PRT
<213> ORGANISM: Artificial sequence
<220> FEATURE:
<223> OTHER INFORMATION: DPO4 Variant

<400> SEQUENCE: 14

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160
```

```
Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Asp Arg Ile Gly Val Arg
                325                 330                 335

Phe Ser Lys Phe
            340

<210> SEQ ID NO 15
<211> LENGTH: 340
<212> TYPE: PRT
<213> ORGANISM: Artificial sequence
<220> FEATURE:
<223> OTHER INFORMATION: DPO4 Variant

<400> SEQUENCE: 15

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175
```

```
Glu Leu Asp Ile Ala Asp Val Leu Gly Ile Pro Tyr Trp Tyr Ala Glu
                180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
        210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Glu Arg Ile Gly Val Arg
                325                 330                 335

Phe Ser Lys Phe
            340

<210> SEQ ID NO 16
<211> LENGTH: 340
<212> TYPE: PRT
<213> ORGANISM: Artificial sequence
<220> FEATURE:
<223> OTHER INFORMATION: DPO4 Variant

<400> SEQUENCE: 16

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190
```

-continued

```
Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Asn Arg Ile Gly Val Arg
                325                 330                 335

Phe Ser Lys Phe
            340

<210> SEQ ID NO 17
<211> LENGTH: 340
<212> TYPE: PRT
<213> ORGANISM: Artificial sequence
<220> FEATURE:
<223> OTHER INFORMATION: DPO4 Variant

<400> SEQUENCE: 17

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205
```

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Leu Arg Ile Gly Val Arg
                325                 330                 335

Phe Ser Lys Phe
            340

<210> SEQ ID NO 18
<211> LENGTH: 340
<212> TYPE: PRT
<213> ORGANISM: Artificial sequence
<220> FEATURE:
<223> OTHER INFORMATION: DPO4 Variant

<400> SEQUENCE: 18

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Glu Ala
        50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
210                 215                 220

```
Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
            245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
            290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Lys Ile Gly Val Arg
            325                 330                 335

Phe Ser Lys Phe
            340

<210> SEQ ID NO 19
<211> LENGTH: 340
<212> TYPE: PRT
<213> ORGANISM: Artificial sequence
<220> FEATURE:
<223> OTHER INFORMATION: DPO4 Variant

<400> SEQUENCE: 19

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Glu Ala
        50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
            130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
            165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240
```

```
Val Arg Lys Ser Ile Gly Arg Thr Val Thr Met Lys Arg Asn Ser Arg
            245                 250                 255

Asn Leu Glu Glu Ile Lys Pro Tyr Leu Phe Arg Ala Ile Glu Glu Ser
        260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
        290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Ala Ile Gly Val Arg
                325                 330                 335

Phe Ser Lys Phe
            340

<210> SEQ ID NO 20
<211> LENGTH: 340
<212> TYPE: PRT
<213> ORGANISM: Artificial sequence
<220> FEATURE:
<223> OTHER INFORMATION: DPO4 Variant

<400> SEQUENCE: 20

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255
```

```
Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Gln Ile Gly Val Arg
                325                 330                 335

Phe Ser Lys Phe
            340

<210> SEQ ID NO 21
<211> LENGTH: 340
<212> TYPE: PRT
<213> ORGANISM: Artificial sequence
<220> FEATURE:
<223> OTHER INFORMATION: DPO4 Variant

<400> SEQUENCE: 21

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270
```

```
Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Ser Ile Gly Val Arg
                325                 330                 335

Phe Ser Lys Phe
            340

<210> SEQ ID NO 22
<211> LENGTH: 340
<212> TYPE: PRT
<213> ORGANISM: Artificial sequence
<220> FEATURE:
<223> OTHER INFORMATION: DPO4 Variant

<400> SEQUENCE: 22

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Glu Ala
        50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285
```

```
Trp Lys Ser Tyr Trp Asn Ser Gln Tyr Arg Trp Ser Trp Phe Pro His
            290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Asn Val Arg
                325                 330                 335

Phe Ser Lys Phe
            340

<210> SEQ ID NO 23
<211> LENGTH: 340
<212> TYPE: PRT
<213> ORGANISM: Artificial sequence
<220> FEATURE:
<223> OTHER INFORMATION: DPO4 Variant

<400> SEQUENCE: 23

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300
```

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gln Val Arg
                325                 330                 335

Phe Ser Lys Phe
            340

<210> SEQ ID NO 24
<211> LENGTH: 340
<212> TYPE: PRT
<213> ORGANISM: Artificial sequence
<220> FEATURE:
<223> OTHER INFORMATION: DPO4 Variant

<400> SEQUENCE: 24

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
                100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
    195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
    275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Phe Val Arg
                325                 330                 335

Phe Ser Lys Phe
            340

<210> SEQ ID NO 25
<211> LENGTH: 340
<212> TYPE: PRT
<213> ORGANISM: Artificial sequence
<220> FEATURE:
<223> OTHER INFORMATION: DPO4 Variant

<400> SEQUENCE: 25

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Ala Val Arg
                325                 330                 335

```
Phe Ser Lys Phe
            340

<210> SEQ ID NO 26
<211> LENGTH: 340
<212> TYPE: PRT
<213> ORGANISM: Artificial sequence
<220> FEATURE:
<223> OTHER INFORMATION: DPO4 Variant

<400> SEQUENCE: 26

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Tyr Lys Phe
            340
```

<210> SEQ ID NO 27
<211> LENGTH: 340
<212> TYPE: PRT
<213> ORGANISM: Artificial sequence
<220> FEATURE:
<223> OTHER INFORMATION: DPO4 Variant

<400> SEQUENCE: 27

```
Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Leu Thr Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Phe Lys Phe
            340
```

<210> SEQ ID NO 28

<211> LENGTH: 340
<212> TYPE: PRT
<213> ORGANISM: Artificial sequence
<220> FEATURE:
<223> OTHER INFORMATION: DPO4 Variant

<400> SEQUENCE: 28

```
Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Leu Gly Ile Pro Tyr Trp Tyr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Ile Gly Val Arg
                325                 330                 335

Phe Ser Lys Phe
            340
```

<210> SEQ ID NO 29
<211> LENGTH: 340
<212> TYPE: PRT
<213> ORGANISM: Artificial sequence
<220> FEATURE:
<223> OTHER INFORMATION: DPO4 Variant

<400> SEQUENCE: 29

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
        50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Gln Gly Ile Pro Tyr Phe Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 30
<211> LENGTH: 340
<212> TYPE: PRT
<213> ORGANISM: Artificial sequence
<220> FEATURE:
<223> OTHER INFORMATION: DPO4 Variant

<400> SEQUENCE: 30

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Cys Val
            20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Arg Ala
        50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Gln Gly Ile Pro Tyr Phe Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Ile Gly Val Arg
                325                 330                 335

Phe Ser Lys Phe
            340

<210> SEQ ID NO 31
<211> LENGTH: 340
<212> TYPE: PRT
<213> ORGANISM: Artificial sequence
<220> FEATURE:
<223> OTHER INFORMATION: DPO4 Variant

<400> SEQUENCE: 31

Met Ile Val Leu Phe Val Asp Phe Asp Tyr Phe Tyr Ala Gln Val Glu

```
  1               5                  10                 15
Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Arg Ala
            50                  55                  60

Lys Lys Ile Leu Pro Asn Ala Val Tyr Leu Pro Trp Arg Asp Leu Val
 65                  70                  75                  80

Tyr Trp Gly Val Ser Glu Arg Ile Met Asn Leu Leu Arg Glu Tyr Ser
                     85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
            130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Glu Val Lys Arg Leu Ile Arg
                    165                 170                 175

Glu Leu Asp Ile Ala Asp Val Gln Gly Ile Pro Tyr Phe Thr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Arg Ser Ile Gly Arg Thr Val Thr Met Lys Arg Asn Ser Arg
                    245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
            290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                    325                 330                 335

Phe Ser Lys Phe
            340

<210> SEQ ID NO 32
<211> LENGTH: 340
<212> TYPE: PRT
<213> ORGANISM: Artificial sequence
<220> FEATURE:
<223> OTHER INFORMATION: DPO4 Variant

<400> SEQUENCE: 32

Met Ile Val Leu Phe Val Asp Phe Asp Tyr Phe Tyr Ala Gln Val Glu
 1               5                  10                  15

Glu Val Leu Asn Pro Ser Leu Lys Gly Lys Pro Val Val Val Cys Val
```

```
                20                  25                  30
Phe Ser Gly Arg Phe Glu Asp Ser Gly Val Val Ala Thr Ala Asn Tyr
            35                  40                  45
Glu Ala Arg Lys Phe Gly Val Tyr Ala Gly Ile Pro Ile Val Arg Ala
        50                  55                  60
Lys Lys Ile Leu Pro Asn Ala Val Tyr Leu Pro Trp Arg Asp Leu Val
65                  70                  75                  80
Tyr Trp Gly Val Ser Glu Arg Ile Met Asn Leu Leu Arg Glu Tyr Ser
                85                  90                  95
Glu Lys Ile Glu Ile Ala Ser Ile Asp Glu Ala Tyr Leu Asp Ile Ser
            100                 105                 110
Asp Lys Val Arg Asp Tyr Arg Glu Ala Tyr Asn Leu Gly Leu Glu Ile
        115                 120                 125
Lys Asn Lys Ile Leu Glu Lys Glu Lys Ile Thr Val Thr Val Gly Ile
130                 135                 140
Ser Lys Asn Lys Val Phe Ala Ala Val Ala Gly Arg Met Ala Lys Pro
145                 150                 155                 160
Asn Gly Ile Lys Val Ile Asp Asp Glu Glu Val Lys Arg Leu Ile Arg
                165                 170                 175
Glu Leu Asp Ile Ala Asp Val Gln Gly Ile Pro Tyr Phe Thr Ala Glu
            180                 185                 190
Lys Leu Lys Lys Leu Gly Ile Asn Lys Leu Val Asp Thr Leu Ser Ile
        195                 200                 205
Glu Phe Asp Lys Leu Lys Gly Met Ile Gly Glu Ala Lys Ala Lys Tyr
210                 215                 220
Leu Ile Ser Leu Ala Arg Asp Glu Tyr Asn Glu Pro Ile Arg Thr Arg
225                 230                 235                 240
Val Arg Lys Ser Ile Gly Arg Thr Val Thr Met Lys Arg Asp Ser Arg
                245                 250                 255
Asn Leu Glu Glu Ile Lys Pro Tyr Leu Phe Arg Ala Ile Glu Glu Ser
            260                 265                 270
Tyr Tyr Lys Leu Asp Lys Arg Ile Pro Lys Ala Ile His Val Val Ala
        275                 280                 285
Trp Lys Ser Tyr Trp Asn Ser Gln Tyr Arg Trp Ser Trp Phe Pro His
290                 295                 300
Gly Ile Ser Lys Glu Thr Ala Tyr Ser Glu Ser Val Gln Leu Leu Gln
305                 310                 315                 320
Gln Ile Leu Lys Lys Asp Lys Arg Lys Ile Arg Arg Ile Gly Val Arg
                325                 330                 335
Phe Ser Lys Phe
            340

<210> SEQ ID NO 33
<211> LENGTH: 340
<212> TYPE: PRT
<213> ORGANISM: Artificial sequence
<220> FEATURE:
<223> OTHER INFORMATION: DPO4 Variant

<400> SEQUENCE: 33

Met Ile Val Leu Phe Val Asp Phe Asp Tyr Phe Tyr Ala Gln Val Glu
1               5                   10                  15
Glu Val Leu Asn Pro Ser Leu Lys Gly Lys Pro Val Val Val Cys Val
            20                  25                  30
Phe Ser Gly Arg Phe Glu Asp Ser Gly Val Val Ala Thr Ala Asn Tyr
```

```
            35                  40                  45

Glu Ala Arg Lys Phe Gly Val Tyr Ala Gly Ile Pro Ile Lys Arg Ala
 50                  55                  60

Lys Lys Ile Leu Pro Asn Ala Val Tyr Leu Pro Trp Arg Asp Leu Val
 65                  70                  75                  80

Tyr Trp Gly Val Ser Glu Arg Ile Met Asn Leu Leu Arg Glu Tyr Ser
                 85                  90                  95

Glu Lys Ile Glu Ile Ala Ser Ile Asp Glu Ala Tyr Leu Asp Ile Ser
                100                 105                 110

Asp Lys Val Arg Asp Tyr Arg Glu Ala Tyr Asn Leu Gly Leu Glu Ile
                115                 120                 125

Lys Asn Lys Ile Leu Glu Lys Glu Lys Ile Thr Val Thr Val Gly Ile
            130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Gln Gly Ile Pro Tyr Phe Thr Ala Glu
                180                 185                 190

Lys Leu Lys Lys Leu Gly Ile Asn Lys Leu Val Asp Thr Leu Ser Ile
                195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
                260                 265                 270

Tyr Tyr Lys Leu Asp Lys Arg Ile Pro Lys Ala Ile His Val Val Ala
            275                 280                 285

Trp Lys Ser Tyr Trp Asn Ser Gln Tyr Arg Trp Ser Trp Phe Pro His
            290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340

<210> SEQ ID NO 34
<211> LENGTH: 340
<212> TYPE: PRT
<213> ORGANISM: Artificial sequence
<220> FEATURE:
<223> OTHER INFORMATION: DPO4 Variant

<400> SEQUENCE: 34

Met Ile Val Leu Phe Val Asp Phe Asp Tyr Phe Tyr Ala Gln Val Glu
  1               5                  10                  15

Glu Val Leu Asn Pro Ser Leu Lys Gly Lys Pro Val Val Val Cys Val
                 20                  25                  30

Phe Ser Gly Arg Phe Glu Asp Ser Gly Val Val Ala Thr Ala Asn Tyr
            35                  40                  45

Glu Ala Arg Lys Phe Gly Val Tyr Ala Gly Ile Pro Ile Val Arg Ala
```

-continued

```
            50                  55                  60
Lys Lys Ile Leu Pro Asn Ala Val Tyr Leu Pro Trp Arg Asp Leu Val
 65              70                  75                      80

Tyr Trp Gly Val Ser Glu Arg Ile Met Asn Leu Leu Arg Glu Tyr Ser
             85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
        130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Gln Gly Ile Pro Tyr Phe Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Arg Ser Ile Gly Arg Thr Val Thr Met Lys Arg Asp Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340
```